US008088727B2

(12) United States Patent
Neufer et al.

(10) Patent No.: US 8,088,727 B2
(45) Date of Patent: Jan. 3, 2012

(54) METHOD FOR REDUCING THE RISK, LESSENING THE SYMPTOM, OR DELAYING THE ONSET OF INSULIN RESISTANCE BY ADMINISTERING SS-31

(75) Inventors: P. Darrell Neufer, Greenville, NC (US); Ethan J. Anderson, Greenville, NC (US); Hazel H. Szeto, New York, NY (US)

(73) Assignees: Cornell University, Ithaca, NY (US); East Carolina University, Greenville, NC (US)

( * ) Notice: Subject to any disclaimer, the term of this patent is extended or adjusted under 35 U.S.C. 154(b) by 0 days.

(21) Appl. No.: 12/367,267

(22) Filed: Feb. 6, 2009

(65) Prior Publication Data
US 2009/0253641 A1 Oct. 8, 2009

Related U.S. Application Data

(60) Provisional application No. 61/026,882, filed on Feb. 7, 2008.

(51) Int. Cl.
*A61K 38/00* (2006.01)
*A61K 38/06* (2006.01)
(52) U.S. Cl. ............ 514/1.1; 514/6.7; 514/6.8; 514/6.9; 514/21.9
(58) Field of Classification Search .................. None
See application file for complete search history.

(56) References Cited

U.S. PATENT DOCUMENTS

| | | | |
|---|---|---|---|
| 5,312,899 A | 5/1994 | Schiller | |
| 5,602,100 A | 2/1997 | Brown et al. | |
| 5,652,122 A | 7/1997 | Frankel et al. | |
| 5,885,958 A | 3/1999 | Zadina et al. | |
| 5,993,848 A | 11/1999 | Suzuki et al. | |
| 5,994,372 A | 11/1999 | Yaksh | |
| 6,221,355 B1 | 4/2001 | Dowdy | |
| 6,258,848 B1 * | 7/2001 | Fantus | 514/562 |
| 6,268,398 B1 | 7/2001 | Ghosh et al. | |
| 6,503,713 B1 | 1/2003 | Rana | |
| 6,703,483 B1 | 3/2004 | Schiller | |
| 6,759,520 B1 | 7/2004 | Carr et al. | |
| 6,900,178 B2 | 5/2005 | Oeltgen et al. | |
| 7,498,297 B2 | 3/2009 | Szeto et al. | |
| 2004/0248808 A1 | 12/2004 | Szeto et al. | |
| 2005/0096333 A1 | 5/2005 | Dugar et al. | |
| 2005/0158373 A1 | 7/2005 | Szeto et al. | |
| 2005/0192215 A1 | 9/2005 | Ghosh et al. | |
| 2006/0084606 A1 | 4/2006 | Szeto | |
| 2007/0015711 A1 | 1/2007 | Szeto et al. | |
| 2007/0027070 A1 | 2/2007 | Szeto et al. | |
| 2007/0027087 A1 | 2/2007 | Szeto et al. | |
| 2007/0093969 A1 | 4/2007 | Mendrick et al. | |
| 2007/0129306 A1 | 6/2007 | Szeto et al. | |
| 2007/0259377 A1 | 11/2007 | Urdea et al. | |
| 2008/0014604 A1 | 1/2008 | Devarajan et al. | |
| 2008/0027082 A1 | 1/2008 | Hocher et al. | |

FOREIGN PATENT DOCUMENTS

| | | |
|---|---|---|
| CA | 2000/2361364 | 9/2000 |
| WO | WO-95/22557 | 8/1995 |
| WO | WO-00/55189 | 9/2000 |
| WO | WO-02/05748 | 1/2002 |
| WO | WO-2004/070054 | 8/2004 |
| WO | WO-2005/001023 | 1/2005 |
| WO | WO-2005/072295 | 8/2005 |
| WO | WO-2007/035640 | 3/2007 |

OTHER PUBLICATIONS

Tataranni (Eur. Rev. for Medical and Pharm. Sci., 2002, 6: 27-32).*
Jain et al (Postgrad Med. J. 72: 365-367, 1996).*
Aitman et al., Identification of CD36 (Fat) as an insulin resistance gene causing defective fatty acid and glucose metabolism in hypertensive rats, Nature Genetics, 21(1):76-83 (1999).
Azzouz, Mimoun, Gene therapy for ALS: progress and prospects, Biochemical et Biophysica Acta, 1762:1122-1127, 2006.
Berendsen, Herman, A glimpse of the holy grail?, Science, 282:642-643, Oct. 23, 1998.
Bickel et al., Synthesis and bioactivity of monobiotinylated DALDA: A Mu-specific opioid peptide designed for targeted brain delivery, J Pharmacol and Exp Therapeutics, 268(2): 791-796 (1994).
Bork et al., Go hunting in sequence databases but watch out for the traps, Trends in Genetics, 12:425-427, 1996.
Bork, Powers and pitfalls in sequence analysis: the 70% hurdle, Genome Research, 10:398-400, 2000.
Bradley et al., Limits of cooperativity in a structurally modular protein: response of the notch ankyrin domain to analogous alanine substitutions in each repeat, J. Mol. Biol., 324:373-386, 2002. Brenner, Errors in genome annotation, Trends in Genetics, 15:132-133, 1999.
Broekemeier et al., Inhibition of the mitochondrial permeability transition by Cyclosporin A during long time frame experiments: relationship between pore opening and the activity of mitochondrial phospholipases, Biochemistry, 34:16440-16449, 1995.
Cho et al., A novel cell-permeable antioxidant peptide, SS31, attenuates ischemic brain injury by down-regulating CD36, J Biol Chem, 282(7): 4634-4642, 2007.
Cho et al., Potent mitochondria-targeted peptides reduce myocardial infarction in rats, Coron Artery Dis., 18(3):215-220, May 2007.
Citron, Martin, Alzheimer's Disease: Treatments in discovery and development, Nature Neuroscience Supplement, 5:1055-1057, Nov. 2002.
Clapp III et al., Cardiovascular and metabolic responses to two receptor-selective opioid agonists in pregnant sheep, American Journal of Obstetrics and Gynecology, 178(2):397-401, Feb. 1998.
Corpeleijin et al. Direct association of a promoter polymorphism in the CD36/FAT fatty acid transporter gene with Type 2 diabetes mellitus and insulin resistance, Diabet Med., 23(8):907-911 (2006).

(Continued)

Primary Examiner — Gyan Chandra
(74) Attorney, Agent, or Firm — Foley & Lardner LLP

(57) ABSTRACT

The invention provides methods of preventing or treating insulin resistance in a mammalian subject. The methods comprise administering to the subject an effective amount of an aromatic-cationic peptide having at least one net positive charge; a minimum of four amino acids; a maximum of about twenty amino acids; a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein $2a$ is the largest number that is less than or equal to $p_t+1$, except that when a is 1, $p_t$ may also be 1.

12 Claims, 12 Drawing Sheets

OTHER PUBLICATIONS

Demas, et al., Anaesthesia for heart transplantation, *Br J. Anaesth*, 58:1357-1564, 1986.

Dimaio et al., Synthesis and pharmacological characterization in vitro of cyclic enkephalin analogues, Effect of Conformational Constraints on Opiate Receptor Selectivity, *J. Med. Chem.*, 25:1432-1438, 1982.

Doerks et al., Protein annotation: detective work for function prediction, *Trends in Genetics*, 14:248-250, 1998.

Dooley, C T et al., Selective ligands for the mu, delta and kappa opioid receptors identified from a single mixture based tetrapeptide positional scanning combinatorial library, *Journal of Biological Chemistry*, American Society of Biochemistry and Molecular Biology, 273(30):18848-18856, Jul. 24, 1998.

Drin et al., Studies on the internalization mechanism of cationic cell-penetrating peptides, *Journal of Biological Chemistry*, 278(33):31192-31201, 2003.

Fuhrman et al., Oxidative stress increases the expression of the CD36 scavenger receptor and the cellular uptake of oxidized low-density lipoprotein in macrophages from atherosclerotic mice: protective role of antioxidants and of paraoxonase, *Atherosclerosis*, 161(2):307-316, Mar. 7, 2002.

Guerrini et al., Opioid receptor selectivity alteration by single residue replacement: synthesis and activity profile of [Dmt] deltorphin B, *European Journal of Pharmacology*, 302:37-42, 1996 (abstract only.).

Herve et al., On the immunogenic properties of retro-inverso peptides. Total retro-inversion of t-cell epitopes causes a loss of binding to MHC II molecules, *Molecular Immunology*, 34(2):157-163, 1997.

Holsey et al., Cardiovascular effects of a μ-selective opioid agonist (Tyrosine-D-Arginine-Phenylalanine-Lysine-NH2) in fetal sheep; Sites and Mechanisms of Action, *Am. J. Obstet. Gynecol.*, 180(5):1127-1130, May 1999.

International Search Report and Written Opinion in International Application No. PCT/US2009/33440, dated Apr. 30, 2009.

Kett et al., Baroreflex-mediated bradycardia but not tachycardia is blunted peripherally by intravenous μ-opioid agonists, *Am. J. Obstet. Gynecol.*, 178(5):950-955, May 1998.

Korczyn et al., Emerging therapies in the pharmacological treatment of Parkinson's Disease, *Drugs*, 62(5):775-786, 2002.

Lasukova et al., Activation of mu-opioid receptors and cardiomyocyte resistance to free radical damage, *Patol Fiziol Eksp Ter.*, 2: English Abstract Only, 2001.

Lishmanov et al., Ligands for opioid and o-receptors improve cardiac electrical stability in rat models of post-infarction cardiosclerosis and stress, *Life Sciences*, 65:13-17, 1999.

Majer et al., Synthesis of methylated phenylalanines via hydrogenolysis of corresponding 1, 2, 3, 4 tetrahydroisoquinoline-3-caraboxylic acids, *Int. Journal of Peptide & Protein Research*, 43:62-68, 1994.

Margolis et al., Diagnosis of Huntington Disease, *Clinical Chemistry*, 49(10):1726-1732, 2003.

Mizuguchi et al., A novel cell-permeable antioxidant peptide decreases renal tubular apoptosis and damage in unilateral ureteral obstruction, *Am J Physiol Renal Physiol.*, 295(5):F1545-1553, Sep. 10, 2008 (epublished).

Moosman et al. Secretory peptide hormones are biochemical antioxidants: structure-activity relationship, *Mol Pharmacol*, 61:260-268, 2002.

Neilan et al., Pharmacological characterization of the dermorphin analog [Dmt1]DALDA, a highly potent and selective u-opioid peptide, *European Journal of Pharmacology*, 419(1):15-23, 2001.

Ngo et al., Computational complexity, protein structure prediction, and the leventhal paradox, the protein folding problem and tertiary structure prediction, (Ed. K. Merz Jr. and S. Le Grand), Birkhauser Boston, 492-495, 1994.

Omoniyi et al., A peripheral site of action for the attenuation of baroreflex-mediated bradycardia by intravenous μ-opioid agonists, *Journal of Cardiovascular PharmocolgyTM*, 35(2):269-274, 2000.

Pages et al., Cystamine and cysteamine increase brain levels of BDNF in Huntington Disease via HSJ1b and transglutaminase, *Journal of Clinical Investigation*, 116(5):1410-1424, May 2006.

Patel et al., Pharmacotherapy of cognitive impairment in Alzheimer's Disease: a review, *J. Geriatr. Psychiatry Neurol.*, 8:81-95, 1995.

Petri et al., Cell-permeable peptide antioxidants as a novel therapeutic approach in a mouse model of amyotrophic lateral sclerosis, *J Neurochem.*, 98(4):1141-1148, Aug. 2006.

Richard et al., Cell-penetrating peptides, *Journal of Biological Chemistry*, 278(1):585-590, 2003.

Rudinger, J., Peptide hormones, (Ed. J. A. Parson), University Park Press, Baltimore, 1-7, 1976.

Schiller et al., Dermorphin analogues carrying an increased positive net charge in their "message" domain display extremely high μ-opioid receptor selectivity, *Journal of Medicinal Chemistry*, 32(3):698-703, 1989.

Schiller et al., Opioid peptide analogs with novel activity profiles as potential therapeutic agents for use in analgesia, 1st Int. Pept. Symp., Program and Abstracts, 0-36, o. 77, 1997.

Schiller et al., Opioid peptide analogs with novel activity profiles as potential therapeutic agents for use in analgesia, Peptide Science-Present and Future, Proc. 1st Int. Pept. Symp., 665-669, 1999.

Schiller et al., Synthesis and in vitro opioid activity profiles of DALDA analogues, European *Journal of Medicinal Chemistry*, 35(10):895-901, Oct. 2000.

Schiller et al., Tipp: A highly potent and stable pseudopeptide opioid receptor antagonist with extraordinary selectivity, *J. Med. Chem.*, 36:3182-3187, 1993.

Schiller et al., Unsulfated C-terminal 7-peptide of cholecystokinin: a new ligand of the opiate receptor, *Biochemical and Biophysical Research Communications*, 85:1332-1338, 1978.

Schiller, P. W. et al., Opioid peptide analogs with novel activity profiles as potential therapeutic agents for use in analgesia, *Stn Caplus*, 132:102403, 1997.

Schwarze, Steven R., et al., In vivo protein transduction: intracellular delivery of biologically active proteins, compounds and DNA, *Trends in Pharmacological Sciences*, 21:45-48, 2000.

Shimoyama, et al., Antinociceptive and respiratory effects of intrathecal H-Tyr-D-Arg-Phe-Lys-NH2 (DALDA) and [Dmtl] DALDA, *The Journal of Pharmacology and Experimental Therapeutics*, 297(1):364-371, Apr. 2001.

Shroff et al., Effects of intrathecal opioid on extubation time, analgesia and intensive care unit stay following coronary artery bypass grafting, *Journal of Clinical Anesthesia*, 9:415-419, 1997.

Simmons, Zachary, Management strategies for patients with Amyotrophic Lateral Sclerosis from diagnosis through death. *The Neurologist*, 11(5):257-270, Sep. 2005 (abstract only) (File Medline on STN. An No. 2005478947).

Skolnick et al., From genes to protein structure and function: novel applications of computational approaches in the genomic era, *Trends in Biotech*, 18(1):34-39, 2000.

Smith et al., The challenges of genome sequence annotation or the devil is in the details, *Nature Biotechnology*, 15:1222-1223, 1997.

Song et al., A potent opiate agonist protects against myocardial stunning during myocardial ischemia and reperfusion in rats, *Coronary Artery Disease*, 16:407-410, 2005.

Spetea, Mariana et al., Interaction of agonist peptides (3H) Tyr-D-Ala-Phe-Phe-NH2 with mu-opioid receptor in rat brain and CHO-mu/1 cell line, *Peptides*, 19(6):1091-1098, 1998.

Sriram et al., Experimental allergic encephalomyelitis: a misleading model of Multiple Sclerosis, *Ann. Neurol.*, 58:939-945, 2005.

Steinman et al., How to successfully apply animal studies in experimental allergic encephalomyelitis to research on Multiple Sclerosis, *Ann. Neurol.*, 60:12-21, 2006.

Szeto et al., In vivo disposition of dermorphin analog (DALDA) in nonpregnant and pregnant sheep, *The Journal of Pharmacology and Experimental Therapeutics*, 284(1):61-65, 1998.

Szeto et al., In vivo pharmacokinetics of selective u-opioid peptide agonists, *The Journal of Pharmacology and Experimental Therapeutics*, 298(1):57-61, Jul. 2001.

Szeto et al., Mu-opioid receptor densensitization and resensitization in vivo, International Narcotics Research Conference, Poster Abstracts, Monday, Mon19:5, 1999.

Szeto et al., Respiratory depression after intravenous administration of o-Selective opioid peptide analogs, *Peptides*, 20:101-105, 1999.

Szeto, Hazel H. Cell-permeable, mitochondrial-targeted, peptide antioxidants, *The AAPS Journal*, 8(2): E277-E283, 2006.

Szeto, Hazel H. Mitochondria-targeted peptide antioxidants: Novel Neuroprotective Agents, *The AAPS Journal*, 8(3): E521-E531, 2006.

Szeto, Hazel H., Development of mitochondria-targeted aromatic-cationic peptides for neurodegenerative diseases, *Annals of the New York Academy of Sciences*, 1147:112-121, 2008.

Szeto, Hazel H., Mitochondria-targeted cytoprotective peptides for ischemia-reperfusion injury, *Antioxid Redox Signal*, 10(3):601-619, 2008.

Thomas et al., Mitochondrial targeting with antioxidant peptide SS-31 prevents mitochondrial depolarization, reduces islet cell apoptosis, increases islet cell yield, and improves posttransplantation function, *J Am Soc Nephrol*, 18: 213-222, 2007.

Thomas et al.,Increased islet yield and reduced apoptosis by prevention of mitochondrial depolarization with cell permeable peptide D-Arg-Dmt-Lys-Phe-NH2. World Transplant Congress 2006. *Am J of Transplantation*, 6(s2)991-992, Abstract #2842 (2006).

Unger et al. Hyperglycaemia as an inducer as well as a consequence of impaired islet cell function and insulin resistance: implications for the management of diabetes, *Diabetologia*, 28(3):119-121 (1985).

Wells, James A., Additivity of mutational effects in proteins, Biochemistry, *American Chemical Society*, 29(37):8509-8517 Sep. 18, 1990.

Wu et al., Myocardial protective effect of mu opioid agonists, International Narcotics Research Conference, Poster Abstracts, Sun59:15, 1999.

Wu, et al., A highly potent peptide analgesic that protects against ischemia-reperfusion-induced myocardial stunning, *Am J Physiol Heart Circ Physiol*, 283:H783-H791, 2002.

Yang et al., Mitochondria targeted peptides protect against 1-methyl-4-phenyl-1, 2, 3, 6-tetrahydropyridine neurotoxicity, *Antioxid Redox Signal*, 2009 (epublished ahead of print).

Zadina, J. et al., A potent and selective endogenous agonist for the mu-opiate receptor, *Nature*, 386:499-502, Apr. 3, 1997.

Zhao et al., Cell-permeable peptide antioxidants targeted to inner mitochondrial membrane inhibit mitochondrial swelling, oxidative cell death, and reperfusion injury, *J. Biol. Chem.*, 279(33):34682-34690, Aug. 2004.

Zhao et al., Mitochondrial-targeted peptide prevents mitochondrial depolarization and apoptosis induced by tert-butyl hydroperoxide in neuronal cell lines, *Biochem Pharmacol.*, 70(12):1796-1806, Oct. 10, 2005 (epublished).

Zhao, Guo-Min et al., Profound spinal tolerance after repeated exposure to a highly selective u-opioid peptide agonist: Role of o-opioid receptors, *J Pharma. Exper. Thera.*, 302(1):188-196, 2002.

Zhao, Kesheng et al., Comparison of [Dmt1]DALDA and DAMGO in Binding and G Protein Activation at µ, d, and κ Opioid Receptors, *J. Parmacology and Experimental Therapeutics*, 307(3):947-954, 2003.

Zhao, Kesheng, et al., Transcellular transport of a highly polar 3+ net charge opioid tetrapeptide, *Journal of Pharmacology and Experimental Therapeutics*, 304(1):425-432, 2003.

Zhao, Kesheng, et al., Translocation of a 3+ net charge tetrapeptide across plasma membrane of mammalian cells, abstract published on-line May 1, 2002, World Congress of Pharmacology Meeting, held Jul. 2002.

Anderson et al., "Mitochondrial H2O2 Emission and Cellular State Link Excess Fat Intake to Insulin Resistance in Both Rodents and Humans," The Journal of Clinical Investigation, vol. 119, No. 3, Feb. 2, 2009, pp. 573-581.

Lowell et al., "Mitochondrial Dysfunction and Type 2 Diabetes," Science, vol. 307, No. 5708, Jan. 21, 2005, pp. 384-387.

Cho et al., "A novel cell-permeable antioxidant peptide, SS31, attenuates ischemic brain injury by down-regulating CD36," The Journal of Biological Chemistry, vol. 282, No. 7, Feb. 16, 2007, pp. 4634-4642.

Extended European Search Report issued on European Patent Application 09707235.9, dated Jun. 9, 2011.

Morino et al., "Molecular Mechanisms of Insulin Resistance in Humans and Their Potential Links with Mitochondrial Dysfunction," Diabetes, vol. 55, No. Suppl. 2, Dec. 2006, pp. S9-S15.

Sheu et al., "Targeting antioxidants to mitochondria: A new therapeutic direction," Biochimica et Biophysica ACTA. Molecular Basis of Disease, vol. 1762, No. 2, Feb. 1, 2006, pp. 256-265.

\* cited by examiner

METHOD FOR REDUCING THE RISK, LESSENING THE SYMPTOM, OR DELAYING THE ONSET OF INSULIN RESISTANCE BY ADMINISTERING SS-31

CROSS-REFERENCE TO RELATED APPLICATIONS

This application claims priority to U.S. Provisional Patent Application No. 61/026,882, filed Feb. 7, 2008, the entire contents of which are hereby incorporated by reference in its entirety.

GOVERNMENT RIGHTS

This invention was made with United States Government support awarded under NIH grant DK073488 and DK056112. The United States Government has certain rights in this invention.

TECHNICAL FIELD

The present invention relates generally to the methods of preventing or treating insulin resistance. In particular, the present invention relates to administering aromatic-cationic peptides in effective amounts to prevent or treat insulin resistance in mammalian skeletal muscle tissues.

BACKGROUND

The following description is provided to assist the understanding of the reader. None of the information provided or references cited is admitted to be prior art to the present invention.

Obesity has become a worldwide epidemic, the consequences of which represent a major challenge facing human health in the 21st century. A decrease in the sensitivity of skeletal muscle to insulin is one of the earliest maladies associated with obesity, and its persistence is a prominent risk factor for type II diabetes and cardiovascular disease. The accumulation of lipid in skeletal muscle has long been associated with the development of insulin resistance, a maladaptive response that is currently attributed to the generation and intracellular accumulation of proinflammatory lipid metabolites (e.g., fatty acyl-CoAs, diacylglycerols and/or ceramides) and associated activation of stress-sensitive serine/threonine kinases that antagonize insulin signaling. Skeletal muscle from obese individuals is also characterized by profound reductions in mitochondrial function as evidenced by decreased expression of metabolic genes, reduced respiratory capacity, and mitochondria that are smaller and less abundant, leading to speculation that a decrease in the capacity to oxidize fat due to acquired or inherited mitochondrial insufficiency may be an underlying cause of the lipid accumulation and insulin resistance that develops in various metabolic states.

SUMMARY

The present invention relates generally to the treatment or prevention of insulin resistance in skeletal muscle tissues through administration of therapeutically effective amounts of aromatic-cationic peptides to subjects in need thereof. In particular embodiments, the aromatic-cationic peptides treat or prevent diet-induced insulin resistance by reducing the occurrence of skeletal muscle mitochondrial dysfunction and over-production of reactive oxygen species.

In one aspect, the invention provides a method of treating or preventing insulin resistance and related complications in a mammalian subject, comprising administering to said mammalian subject a therapeutically effective amount of an aromatic-cationic peptide. In some embodiments, the aromatic-cationic peptide is a peptide having:

at least one net positive charge;
a minimum of four amino acids;
a maximum of about twenty amino acids;
a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein 2a is the largest number that is less than or equal to $p_t$+1, except that when a is 1, $p_t$ may also be 1. In particular embodiments, the mammalian subject is a human.

In one embodiment, $2p_m$ is the largest number that is less than or equal to r+1, and a may be equal to $p_t$. The aromatic-cationic peptide may be a water-soluble peptide having a minimum of two or a minimum of three positive charges.

In one embodiment, the peptide comprises one or more non-naturally occurring amino acids, for example, one or more D-amino acids. In some embodiments, the C-terminal carboxyl group of the amino acid at the C-terminus is amidated. In certain embodiments, the peptide has a minimum of four amino acids. The peptide may have a maximum of about 6, a maximum of about 9, or a maximum of about 12 amino acids.

In some embodiments, the peptide has opioid receptor agonist activity. In other embodiments, the peptide does not have opioid receptor agonist activity.

In one embodiment, the peptide comprises a tyrosine or a 2',6'-dimethyltyrosine (Dmt) residue at the N-terminus. For example, the peptide may have the formula Tyr-D-Arg-Phe-Lys-NH$_2$ (SS-01) or 2',6'-Dmt-D-Arg-Phe-Lys-NH$_2$ (SS-02). In another embodiment, the peptide comprises a phenylalanine or a 2',6'-dimethylphenylalanine residue at the N-terminus. For example, the peptide may have the formula Phe-D-Arg-Phe-Lys-NH$_2$ (SS-20) or 2',6'-Dmp-D-Arg-Phe-Lys-NH$_2$. In a particular embodiment, the aromatic-cationic peptide has the formula D-Arg-2'6'Dmt-Lys-Phe-NH$_2$ (SS-31).

In one embodiment, the peptide is defined by formula I:

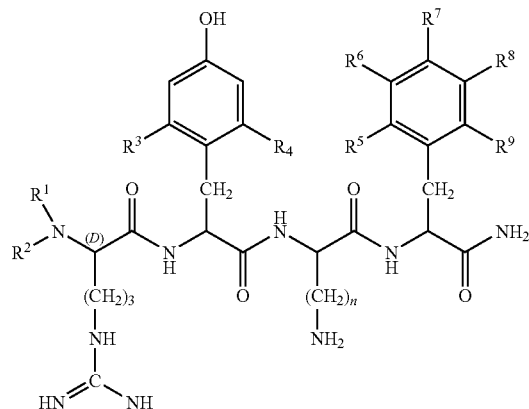

wherein R$^1$ and R$^2$ are each independently selected from
(i) hydrogen;
(ii) linear or branched C$_1$-C$_6$ alkyl;

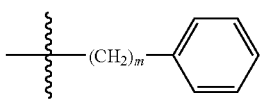

where m=1-3;

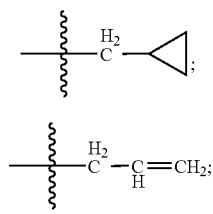

R³ and R⁴ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo;
R⁵, R⁶, R⁷, R⁸, and R⁹ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo; and n is an integer from 1 to 5.

In a particular embodiment, R¹ and R² are hydrogen; R³ and R⁴ are methyl; R⁵, R⁶, R⁷, R⁸, and R⁹ are all hydrogen; and n is 4.

In some embodiments, the aromatic-cationic peptides of the invention are used to treat or prevent complications related to insulin resistance in mammalian subjects, which include, but are not limited to, hyperinsulinemia, type II diabetes, abnormal lipid metabolism, abnormal vascular endothelial function, retinopathy, coronary artery disease, cardiovascular disease, renal dysfunction, hypertension, fatty liver, neuropathy, and hyperuricemia. Specific examples of cardiovascular disease potentially caused by long-term insulin resistance include myocardial infarction, hemorrhagic or ischemic stroke (cerebral infarction).

The aromatic-cationic peptides of the invention may be administered in a variety of ways. In some embodiments, the peptides may be administered orally, topically, intranasally, intravenously, subcutaneously, or transdermally (e.g., by iontophoresis).

In another aspect, the invention provides a method of preventing and/or treating diabetes, obesity, hyperlipemia, arteriosclerosis, cerebrovascular disease, hypertension or heart disease comprising administering a therapeutically effective amount of aromatic-cationic peptides to subjects in need thereof. In a particular embodiment, the aromatic-cationic peptide comprises D-Arg-2'6'Dmt-Lys-Phe-NH₂ (SS-31).

BRIEF DESCRIPTION OF THE FIGURES

FIG. 1A is a representative trace comparing rates of mitochondrial $H_2O_2$ emission from permeabilized skeletal muscle fibers prepared from rats fed standard chow, high fat chow for 3 days, or high fat chow 3 weeks. FIG. 1B is a graph showing the mitochondrial oxidant emitting potential of permeabilized rat skeletal myofibers in control rats fed a normal diet and rats fed a high fat diet.

FIGS. 3A and 3B are graphs showing dose response curves of SS-31 antioxidant activity in vitro and in vivo, respectively. FIGS. 3C and 3D are graphs showing the mitochondrial oxidant emitting potential of permeabilized rat skeletal myofibers in control rats fed standard chow, a high fat diet, or a high fat diet with daily SS-31 administration and assayed for succinate-stimulated $H_2O_2$ emission (FIG. 3C) and palmitoyl-carnitine stimulated $H_2O_2$ emission (FIG. 3D). FIGS. 3E and 3F are charts showing respiration rates in control rats fed standard chow, a high fat diet, or a high fat diet with daily SS-31 administration. Respiration was measured with pyruvate and malate (FIG. 3E) or palmitoyl-carnitine and malate (FIG. 3F) in both basal ($PM_4$, $PCM_4$) and maximal ADP-stimulated ($PM_3$, $PCM_3$) respiratory states. FIG. 3G is a chart showing total glutathione in control rats fed standard chow, a high fat diet, or a high fat diet with daily SS-31 administration. FIG. 3H is a chart showing the ratio of GSH/GSSG in control rats fed standard chow, a high fat diet, or a high fat diet with daily SS-31 administration. Analyses were performed either before (−) or 1 h after (+) oral glucose ingestion. Data are representative of mean ±S.E.M.; n=4-6, * $P<0.05$ vs. Ctl-Std chow, †$P<0.05$ vs. SS-31 treated.

FIG. 4A is a graph showing plasma glucose clearance rate in control rats fed standard chow, a high fat diet, or a high fat diet with daily SS-31 administration. FIG. 4B is a graph showing fasting plasma insulin levels in the same experimental subjects. FIG. 4C is a chart showing increased homeostatic model assessment (HOMA) and FIG. 4D is a chart showing greater area under the curve (AUC) for both glucose and insulin in control rats fed standard chow, a high fat diet, or a high fat diet with daily SS-31 administration. Data are representative of mean ±S.E.M.; n=9-10, * $P<0.05$ vs. Ctl-Std chow, †$P<0.05$ vs. SS31 treated. FIG. 4E is an immunoblot of phosphorylated Akt and total Akt in rat skeletal muscle homogenates in response to glucose challenge.

FIGS. 5A and 5B are graphs showing mitochondrial $H_2O_2$ emission from permeabilized fibers prepared from biopsies obtained from vastus lateralis of obese and lean human males. Both succinate-supported (FIG. 5A) and palmitoyl-carnitine supported (FIG. 5B) $H_2O_2$ emission were measured. FIG. 5C is a graph showing the ratio of $H_2O_2$ emitted/$O_2$ consumed in obese samples as compared to lean. FIG. 5D is a graph showing respiration in the presence of glutamate/malate ($GM_4$), ADP ($GM_3$), and palmitoyl-carnitine/malate in either basal ($PCM_4$) or maximal ($PCM_3$) state. FIG. 5E is a graph showing total glutathione ($GSH_t$) in obese skeletal muscle compared to lean. FIG. 5F is a graph showing the ratio of GSH/GSSG in obese skeletal muscle compared to lean. Data are representative of mean ±S.E.M.; n=4-5, * P<0.05 vs. lean male for that respective experiment.

DETAILED DESCRIPTION

Figure 1A:
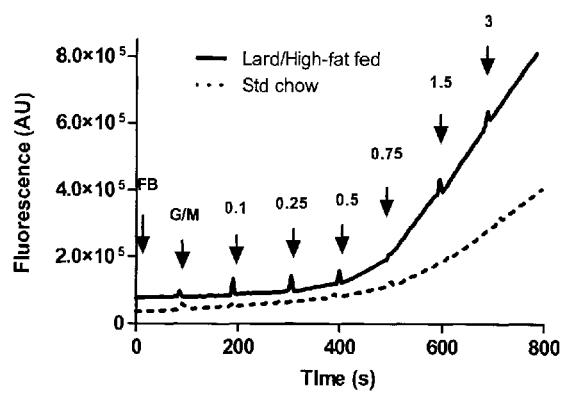
FIGS. 1A-B are a series of graphs showing the impact of excess dietary fat on skeletal muscle mitochondrial $H_2O_2$ emission.

It is to be appreciated that certain aspects, modes, embodiments, variations and features of the invention are described below in various levels of detail in order to provide a substantial understanding of the present invention.

In practicing the present invention, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzymol.*, Vols. 154 and 155, Wu & Grossman, and Wu, Eds., respectively. Methods to detect and measure levels of polypeptide gene expression products (i.e., gene translation level) are well-known in the art and include the use polypeptide detection methods such as antibody detection and quantification techniques. (See also, Strachan & Read, *Human Molecular Genetics*, Second Edition. (John Wiley and Sons, Inc., NY, 1999)).

The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well known and commonly employed in the art.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "biological sample" means sample material derived from or contacted by living cells. The term "biological sample" is intended to include tissues, cells and biological fluids isolated from a subject, as well as tissues, cells and fluids present within a subject. Biological samples of the invention include, e.g., but are not limited to, whole blood, plasma, semen, saliva, tears, urine, fecal material, sweat, buccal, skin, cerebrospinal fluid, and hair. Biological samples can also be obtained from biopsies of internal organs or from cancers. Biological samples can be obtained from subjects for diagnosis or research or can be obtained from undiseased individuals, as controls or for basic research.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with insulin resistance. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds. In the methods of the present invention, the aromatic-cationic peptides may be administered to a subject having one or more signs of insulin resistance caused by a disease or condition. Administration of an effective amount of the aromatic-cationic peptides may improve at least one sign or symptom of insulin resistance in the subject, e.g., body weight, fasting glucose/insulin/free fatty acid, glucose tolerance (OGTT), in vitro muscle insulin sensitivity, markers of insulin signaling (e.g., Akt-P, IRS-P), mitochondrial function (e.g., respiration or $H_2O_2$ emission), markers of intracellular oxidative stress (e.g., lipid peroxidation, GSH/GSSG ratio or aconitase activity) and mitochondrial enzyme activity. For example, a "therapeutically effective amount" of the aromatic-cationic peptides is meant levels in which the physiological effects of insulin resistance are, at a minimum, ameliorated.

An "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, the term "medical condition" includes, but is not limited to, any condition or disease manifested as one or more physical and/or psychological symptoms for which treatment and/or prevention is desirable, and includes previously and newly identified diseases and other disorders. For example, a medical condition may be insulin resistance, hyperinsulinemia, type II diabetes, abnormal lipid metabolism, abnormal vascular endothelial function, coronary artery disease, cardiovascular disease, cerebrovascular disease, renal dysfunction, hypertension, fatty liver, neuropathy, and hyperuricemia.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for insulin resistance if, after receiving a therapeutic amount of the aromatic-cationic peptides according to the methods of the present invention, the subject shows observable and/or measurable reduction in or absence of one or more signs and symptoms of a particular disease or condition. For example, for insulin resistance, treatment may include a reduction in the fasting blood glucose or insulin levels, or the areas under the curve for glucose and insulin in response to oral glucose challenge. It is also to be appreciated that the various modes of treatment or prevention of medical conditions as described are intended to mean "substantial", which includes total but also less than total treatment or prevention, and wherein some biologically or medically relevant result is achieved.

The present inventors have discovered that, surprisingly, aromatic-cationic peptides can prevent or treat insulin resistance in mammalian tissues; in particular, insulin resistance in skeletal muscle tissues. In some cases, the insulin resistance may be due to a high fat diet or, more generally, overnutrition. The peptides of the invention are beneficial in treating diabetic, pre-diabetic or obese insulin resistant, non-diabetic patients. Without intending to limit the invention to a particular mechanism of action, it is believed that loss of mitochondrial integrity and insulin sensitivity stem from a common metabolic disturbance, i.e., oxidative stress. Overnutrition, particularly from high fat diets may increase mitochondrial reactive oxygen species (ROS) emission and overall oxidative stress in skeletal muscle, leading to both acute and chronic mitochondrial dysfunction and the development of insulin resistance. The aromatic-cationic peptides of the present invention mitigate these effects, thereby improving mitochondrial function in skeletal muscle tissues, thus improving insulin sensitivity. The invention also provides methods of using peptides of the invention to prevent or treat diabetes, pre-diabetes, related metabolic diseases, and complications arising therefrom.

The present inventors found that high fat diet/obesity-induced insulin resistance is related to mitochondrial bioenergetics. The implication is that the oversupply of metabolic substrates causes the mitochondrial respiratory system to become more reduced, generating an increase in ROS emission and shift in the overall redox environment to a more oxidized state that, if persistent, leads to development of insulin resistance. Linking mitochondrial bioenergetics to the etiology of insulin resistance has a number of clinical implications. It is known that standard care of insulin resistance (NIDDM) in humans often results in weight gain and, in selected individuals, increased variability of blood sugar with resulting metabolic and clinical consequences. The examples shown herein demonstrate that treatment of mitochondrial defect with mitochondrial-targeted antioxidant (e.g. an aromatic cationic peptide) provides a new and surprising approach to metabolic correction of insulin resistance without the growth and metabolic effects of increased insulin.

The present invention relates to the reduction of insulin resistance by certain aromatic-cationic peptides. The aromatic-cationic peptides are water-soluble and highly polar. Despite these properties, the peptides can readily penetrate cell membranes. The aromatic-cationic peptides useful in the present invention include a minimum of three amino acids, and preferably include a minimum of four amino acids, covalently joined by peptide bonds. The maximum number of amino acids present in the aromatic-cationic peptides of the present invention is about twenty amino acids covalently joined by peptide bonds. Preferably, the maximum number of amino acids is about twelve, more preferably about nine, and most preferably about six. Optimally, the number of amino acids present in the peptides is four.

The amino acids of the aromatic-cationic peptides useful in the present invention can be any amino acid. As used herein, the term "amino acid" is used to refer to any organic molecule that contains at least one amino group and at least one carboxyl group. Preferably, at least one amino group is at the α position relative to a carboxyl group. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid include hydroxyproline (Hyp).

The peptides useful in the present invention optionally contain one or more non-naturally occurring amino acids. Optimally, the peptide has no amino acids that are naturally occurring. The non-naturally occurring amino acids may be levorotary (L-), dextrorotatory (D-), or mixtures thereof. Non-naturally occurring amino acids are those amino acids that typically are not synthesized in normal metabolic processes in living organisms, and do not naturally occur in proteins. In addition, the non-naturally occurring amino acids useful in the present invention preferably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ε-aminocaproic acid. Some examples of non-natural aryl amino acids include ortho-, meta, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide useful in the methods of the present invention is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are preferably resistant, and more preferably insensitive, to common proteases. Examples of non-naturally occurring amino acids that are resistant or insensitive to proteases include the dextrorotatory (D-) form of any of the above-mentioned naturally occurring L-amino acids, as well as L-and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides useful in the methods of the invention should have less than five, preferably less than four, more preferably less than three, and most preferably, less than two contiguous L-amino acids recognized by common proteases, irrespective of whether the amino acids are naturally or non-naturally occurring. Optimally, the peptide has only D-amino acids, and no L-amino acids. If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-D-Arg has one negatively charged amino acid (i.e., Glu) and four positively charged amino acids (i.e., two Arg residues, one Lys, and one His). Therefore, the above peptide has a net positive charge of three.

In one embodiment of the present invention, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 1

| Amino acid number and net positive charges ($3p_m \leq p + 1$) | | | | | | | | | | | | | | | | | |
|---|---|---|---|---|---|---|---|---|---|---|---|---|---|---|---|---|---|
| (r) | | | | | | | | | | | | | | | | | |
| 3 | 4 | 5 | 6 | 7 | 8 | 9 | 10 | 11 | 12 | 13 | 14 | 15 | 16 | 17 | 18 | 19 | 20 |
| ($p_m$) 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

Amino acid number and net positive charges ($2p_m \leq p + 1$)

| | | | | | | | | (r) | | | | | | | | | | |
|---|---|---|---|---|---|---|---|---|---|---|---|---|---|---|---|---|---|---|
| | 3 | 4 | 5 | 6 | 7 | 8 | 9 | 10 | 11 | 12 | 13 | 14 | 15 | 16 | 17 | 18 | 19 | 20 |
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, preferably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups will be referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides useful in the methods of the present invention should also have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

TABLE 3

Aromatic groups and net positive charges ($3a \leq p_t + 1$ or $a = p_t = 1$)

| | | | | | | | | ($p_t$) | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t$+1. In this embodiment, the relationship between the minimum number of aromatic amino acid residues (a) and the total number of net positive charges ($p_t$) is as follows:

TABLE 4

Aromatic groups and net positive charges ($3a \leq p_t + 1$ or $a = p_t = 1$)

| | | | | | | | | ($p_t$) | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, are preferably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides of the present invention may also be amidated wherever they occur within the peptide. The amidation at these internal positions may be with ammonia or any of the primary or secondary amines described above.

In one embodiment, the aromatic-cationic peptide useful in the methods of the present invention is a tripeptide having two net positive charges and at least one aromatic amino acid. In a particular embodiment, the aromatic-cationic peptide useful in the methods of the present invention is a tripeptide having two net positive charges and two aromatic amino acids.

Aromatic-cationic peptides useful in the methods of the present invention include, but are not limited to, the following peptide examples:

```
Lys-D-Arg-Tyr-NH2

Phe-D-Arg-His

D-Tyr-Trp-Lys-NH2

Trp-D-Lys-Tyr-Arg-NH2

Tyr-His-D-Gly-Met

Phe-Arg-D-His-Asp

Tyr-D-Arg-Phe-Lys-Glu-NH2

Met-Tyr-D-Lys-Phe-Arg

D-His-Glu-Lys-Tyr-D-Phe-Arg

Lys-D-Gln-Tyr-Arg-D-Phe-Trp-NH2

Phe-D-Arg-Lys-Trp-Tyr-D-Arg-His

Gly-D-Phe-Lys-Tyr-His-D-Arg-Tyr-NH2

Val-D-Lys-His-Tyr-D-Phe-Ser-Tyr-Arg-NH2

Trp-Lys-Phe-D-Asp-Arg-Tyr-D-His-Lys

Lys-Trp-D-Tyr-Arg-Asn-Phe-Tyr-D-His-NH2

Thr-Gly-Tyr-Arg-D-His-Phe-Trp-D-His-Lys

Asp-D-Trp-Lys-Tyr-D-His-Phe-Arg-D-Gly-Lys-NH2

D-His-Lys-Tyr-D-Phe-Glu-D-Asp-D-His-D-Lys-Arg-Trp-NH2

Ala-D-Phe-D-Arg-Tyr-Lys-D-Trp-His-D-Tyr-Gly-Phe

Tyr-D-His-Phe-D-Arg-Asp-Lys-D-Arg-His-Trp-D-His-Phe

Phe-Phe-D-Tyr-Arg-Glu-Asp-D-Lys-Arg-D-Arg-His-Phe-NH2

Phe-Try-Lys-D-Arg-Trp-His-D-Lys-D-Lys-Glu-Arg-D-Tyr-Thr

Tyr-Asp-D-Lys-Tyr-Phe-D-Lys-D-Arg-Phe-Pro-D-Tyr-His-Lys

Glu-Arg-D-Lys-Tyr-D-Val-Phe-D-His-Trp-Arg-D-Gly-Tyr-Arg-D-Met-NH2

Arg-D-Leu-D-Tyr-Phe-Lys-Glu-D-Lys-Arg-D-Trp-Lys-D-Phe-Tyr-D-Arg-Gly

D-Glu-Asp-Lys-D-Arg-D-His-Phe-Phe-D-Val-Tyr-Arg-Tyr-D-Tyr-Arg-His-Phe-
NH2

Asp-Arg-D-Phe-Cys-Phe-D-Arg-D-Lys-Tyr-Arg-D-Tyr-Trp-D-His-Tyr-D-Phe-Lys-
Phe

His-Tyr-D-Arg-Trp-Lys-Phe-D-Asp-Ala-Arg-Cys-D-Tyr-His-Phe-D-Lys-Tyr-His-
Ser-NH2

Gly-Ala-Lys-Phe-D-Lys-Glu-Arg-Tyr-His-D-Arg-D-Arg-Asp-Tyr-Trp-D-His-Trp-
His-D-Lys-Asp

Thr-Tyr-Arg-D-Lys-Trp-Tyr-Glu-Asp-D-Lys-D-Arg-His-Phe-D-Tyr-Gly-Val-Ile-D-
His-Arg-Tyr-Lys-NH2
```

In one embodiment, the peptides useful in the methods of the present invention have mu-opioid receptor agonist activity (i.e., they activate the mu-opioid receptor). Mu-opioid activity can be assessed by radioligand binding assay to cloned mu-opioid receptors or by bioassays suing the guinea pig ileum (Schiller et al., *Eur J Med Chem,* 35:895-901, 2000; Zhao et al., *J Pharmacol Exp Ther* 307:947-954, 2003). Activation of the mu-opioid receptor typically elicits an analgesic effect. In certain instances, an aromatic-cationic peptide having mu-opioid receptor agonist activity is preferred. For example, during short-term treatment, such as in an acute disease or condition, it may be beneficial to use an aromatic-cationic peptide that activates the mu-opioid receptor. Such acute diseases and conditions are often associated with moderate or severe pain. In these instances, the analgesic effect of the aromatic-cationic peptide may be beneficial in the treatment regimen of the human patient or other mammal. An aromatic-cationic peptide which does not activate the mu-opioid receptor, however, may also be used with or without an analgesic, according to clinical requirements.

Alternatively, in other instances, an aromatic-cationic peptide that does not have mu-opioid receptor agonist activity is preferred. For example, during long-term treatment, such as in a chronic disease state or condition, the use of an aromatic-cationic peptide that activates the mu-opioid receptor may be contraindicated. In these instances the potentially adverse or addictive effects of the aromatic-cationic peptide may preclude the use of an aromatic-cationic peptide that activates the mu-opioid receptor in the treatment regimen of a human patient or other mammal. Potential adverse effects may include sedation, constipation and respiratory depression. In such instances an aromatic-cationic peptide that does not activate the mu-opioid receptor may be an appropriate treatment.

Peptides useful in the methods of the present invention which have mu-opioid receptor agonist activity are typically those peptides which have a tyrosine residue or a tyrosine derivative at the N-terminus (i.e., the first amino acid position). Preferred derivatives of tyrosine include 2'-methyltyrosine (Mmt); 2',6'-dimethyltyrosine (2'6'Dmt); 3',5'-dimethyltyrosine (3'5'Dmt); N,2',6'-trimethyltyrosine (Tmt); and 2'-hydroxy-6'-methyltyrosine (Hmt).

In one embodiment, a peptide that has mu-opioid receptor agonist activity has the formula Tyr-D-Arg-Phe-Lys-NH$_2$ (referred to herein as "SS-01"). SS-01 has a net positive charge of three, contributed by the amino acids tyrosine, arginine, and lysine and has two aromatic groups contributed by the amino acids phenylalanine and tyrosine. The tyrosine of SS-01 can be a modified derivative of tyrosine such as in 2',6'-dimethyltyrosine to produce the compound having the formula 2',6'-Dmt-D-Arg-Phe-Lys-NH$_2$ (referred to herein as "SS-02"). SS-02 has a molecular weight of 640 and carries a net three positive charge at physiological pH. SS-02 readily penetrates the plasma membrane of several mammalian cell types in an energy-independent manner (Zhao et al., *J. Pharmacol Exp Ther.* 304: 425-432, 2003).

Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (Dmp), N,2',6'-trimethylphenylalanine (Tmp), and 2'-hydroxy-6'-methylphenylalanine (Hmp).

An example of a aromatic-cationic peptide that does not have mu-opioid receptor agonist activity has the formula Phe-D-Arg-Phe-Lys-NH$_2$ (referred to herein as "SS-20"). Alternatively, the N-terminal phenylalanine can be a derivative of phenylalanine such as 2',6'-dimethylphenylalanine (2'6'Dmp). SS-01 containing 2',6'-dimethylphenylalanine at amino acid position 1 has the formula 2',6'-Dmp-D-Arg-Phe-Lys-NH$_2$. In one embodiment, the amino acid sequence of SS-02 is rearranged such that Dmt is not at the N-terminus. An example of such an aromatic-cationic peptide that does not have mu-opioid receptor agonist activity has the formula D-Arg-2'6'Dmt-Lys-Phe-NH$_2$ (SS-31).

SS-01, SS-20, SS-31, and their derivatives can further include functional analogs. A peptide is considered a functional analog of SS-01, SS-20, or SS-31 if the analog has the same function as SS-01, SS-20, or SS-31. The analog may, for example, be a substitution variant of SS-01, SS-20, or SS-31, wherein one or more amino acids are substituted by another amino acid.

Suitable substitution variants of SS-01, SS-20, or SS-31 include conservative amino acid substitutions. Amino acids may be grouped according to their physicochemical characteristics as follows:

(a) Non-polar amino acids: Ala(A) Ser(S) Thr(T) Pro(P) Gly(G) Cys (C);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val (V); and
(e) Aromatic amino acids: Phe(F) Tyr(Y) Trp(W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group is generally more likely to alter the characteristics of the original peptide.

In some embodiments, one or more naturally occurring amino acids in the aromatic-cationic peptides are substituted with amino acid analogs. Examples of analogs useful in the practice of the present invention that activate mu-opioid receptors include, but are not limited to, the aromatic-cationic peptides shown in Table 5.

TABLE 5

Peptide Analogs with Mu-Opioid Activity

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| Tyr | D-Arg | Phe | Lys | | NH$_2$ |
| Tyr | D-Arg | Phe | Orn | | NH$_2$ |
| Tyr | D-Arg | Phe | Dab | | NH$_2$ |
| Tyr | D-Arg | Phe | Dap | | NH$_2$ |
| 2'6'Dmt | D-Arg | Phe | Lys | | NH$_2$ |

TABLE 5-continued

Peptide Analogs with Mu-Opioid Activity

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| 2'6'Dmt | D-Arg | Phe | Lys-NH(CH$_2$)$_2$—NH-dns | | NH$_2$ |
| 2'6'Dmt | D-Arg | Phe | Lys-NH(CH$_2$)$_2$—NH-atn | | NH$_2$ |
| 2'6'Dmt | D-Arg | Phe | dnsLys | | NH$_2$ |
| 2'6'Dmt | D-Cit | Phe | Lys | | NH$_2$ |
| 2'6'Dmt | D-Cit | Phe | Ahp | | NH$_2$ |
| 2'6'Dmt | D-Arg | Phe | Orn | | NH$_2$ |
| 2'6'Dmt | D-Arg | Phe | Dab | | NH$_2$ |
| 2'6'Dmt | D-Arg | Phe | Dap | | NH$_2$ |
| 2'6'Dmt | D-Arg | Phe | Ahp(2-aminoheptanoic acid) | | NH$_2$ |
| Bio-2'6'Dmt | D-Arg | Phe | Lys | | NH$_2$ |
| 3'5'Dmt | D-Arg | Phe | Lys | | NH$_2$ |
| 3'5'Dmt | D-Arg | Phe | Orn | | NH$_2$ |
| 3'5'Dmt | D-Arg | Phe | Dab | | NH$_2$ |
| 3'5'Dmt | D-Arg | Phe | Dap | | NH$_2$ |
| Tyr | D-Arg | Tyr | Lys | | NH$_2$ |
| Tyr | D-Arg | Tyr | Orn | | NH$_2$ |
| Tyr | D-Arg | Tyr | Dab | | NH$_2$ |
| Tyr | D-Arg | Tyr | Dap | | NH$_2$ |
| 2'6'Dmt | D-Arg | Tyr | Lys | | NH$_2$ |
| 2'6'Dmt | D-Arg | Tyr | Orn | | NH$_2$ |
| 2'6'Dmt | D-Arg | Tyr | Dab | | NH$_2$ |
| 2'6'Dmt | D-Arg | Tyr | Dap | | NH$_2$ |
| 2'6'Dmt | D-Arg | 2'6'Dmt | Lys | | NH$_2$ |
| 2'6'Dmt | D-Arg | 2'6'Dmt | Orn | | NH$_2$ |
| 2'6'Dmt | D-Arg | 2'6'Dmt | Dab | | NH$_2$ |
| 2'6'Dmt | D-Arg | 2'6'Dmt | Dap | | NH$_2$ |
| 3'5'Dmt | D-Arg | 3'5'Dmt | Arg | | NH$_2$ |
| 3'5'Dmt | D-Arg | 3'5'Dmt | Lys | | NH$_2$ |
| 3'5'Dmt | D-Arg | 3'5'Dmt | Orn | | NH$_2$ |
| 3'5'Dmt | D-Arg | 3'5'Dmt | Dab | | NH$_2$ |
| Tyr | D-Lys | Phe | Dap | | NH$_2$ |
| Tyr | D-Lys | Phe | Arg | | NH$_2$ |
| Tyr | D-Lys | Phe | Lys | | NH$_2$ |
| Tyr | D-Lys | Phe | Orn | | NH$_2$ |
| 2'6'Dmt | D-Lys | Phe | Dab | | NH$_2$ |
| 2'6'Dmt | D-Lys | Phe | Dap | | NH$_2$ |
| 2'6'Dmt | D-Lys | Phe | Arg | | NH$_2$ |
| 2'6'Dmt | D-Lys | Phe | Lys | | NH$_2$ |
| 3'5'Dmt | D-Lys | Phe | Orn | | NH$_2$ |
| 3'5'Dmt | D-Lys | Phe | Dab | | NH$_2$ |
| 3'5'Dmt | D-Lys | Phe | Dap | | NH$_2$ |
| 3'5'Dmt | D-Lys | Phe | Arg | | NH$_2$ |
| Tyr | D-Lys | Tyr | Lys | | NH$_2$ |
| Tyr | D-Lys | Tyr | Orn | | NH$_2$ |
| Tyr | D-Lys | Tyr | Dab | | NH$_2$ |
| Tyr | D-Lys | Tyr | Dap | | NH$_2$ |
| 2'6'Dmt | D-Lys | Tyr | Lys | | NH$_2$ |
| 2'6'Dmt | D-Lys | Tyr | Orn | | NH$_2$ |
| 2'6'Dmt | D-Lys | Tyr | Dab | | NH$_2$ |
| 2'6'Dmt | D-Lys | Tyr | Dap | | NH$_2$ |
| 2'6'Dmt | D-Lys | 2'6'Dmt | Lys | | NH$_2$ |
| 2'6'Dmt | D-Lys | 2'6'Dmt | Orn | | NH$_2$ |
| 2'6'Dmt | D-Lys | 2'6'Dmt | Dab | | NH$_2$ |
| 2'6'Dmt | D-Lys | 2'6'Dmt | Dap | | NH$_2$ |
| 2'6'Dmt | D-Arg | Phe | dnsDap | | NH$_2$ |
| 2'6'Dmt | D-Arg | Phe | atnDap | | NH$_2$ |
| 3'5'Dmt | D-Lys | 3'5'Dmt | Lys | | NH$_2$ |
| 3'5'Dmt | D-Lys | 3'5'Dmt | Orn | | NH$_2$ |
| 3'5'Dmt | D-Lys | 3'5'Dmt | Dab | | NH$_2$ |
| 3'5'Dmt | D-Lys | 3'5'Dmt | Dap | | NH$_2$ |
| Tyr | D-Lys | Phe | Arg | | NH$_2$ |
| Tyr | D-Orn | Phe | Arg | | NH$_2$ |
| Tyr | D-Dab | Phe | Arg | | NH$_2$ |
| Tyr | D-Dap | Phe | Arg | | NH$_2$ |
| 2'6'Dmt | D-Arg | Phe | Arg | | NH$_2$ |
| 2'6'Dmt | D-Lys | Phe | Arg | | NH$_2$ |
| 2'6'Dmt | D-Orn | Phe | Arg | | NH$_2$ |
| 2'6'Dmt | D-Dab | Phe | Arg | | NH$_2$ |
| 3'5'Dmt | D-Dap | Phe | Arg | | NH$_2$ |
| 3'5'Dmt | D-Arg | Phe | Arg | | NH$_2$ |

TABLE 5-continued

Peptide Analogs with Mu-Opioid Activity

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| 3'5'Dmt | D-Lys | Phe | Arg | | $NH_2$ |
| 3'5'Dmt | D-Orn | Phe | Arg | | $NH_2$ |
| Tyr | D-Lys | Tyr | Arg | | $NH_2$ |
| Tyr | D-Orn | Tyr | Arg | | $NH_2$ |
| Tyr | D-Dab | Tyr | Arg | | $NH_2$ |
| Tyr | D-Dap | Tyr | Arg | | $NH_2$ |
| 2'6'Dmt | D-Arg | 2'6'Dmt | Arg | | $NH_2$ |
| 2'6'Dmt | D-Lys | 2'6'Dmt | Arg | | $NH_2$ |
| 2'6'Dmt | D-Orn | 2'6'Dmt | Arg | | $NH_2$ |
| 2'6'Dmt | D-Dab | 2'6'Dmt | Arg | | $NH_2$ |
| 3'5'Dmt | D-Dap | 3'5'Dmt | Arg | | $NH_2$ |
| 3'5'Dmt | D-Arg | 3'5'Dmt | Arg | | $NH_2$ |
| 3'5'Dmt | D-Lys | 3'5'Dmt | Arg | | $NH_2$ |
| 3'5'Dmt | D-Orn | 3'5'Dmt | Arg | | $NH_2$ |
| Mmt | D-Arg | Phe | Lys | | $NH_2$ |
| Mmt | D-Arg | Phe | Orn | | $NH_2$ |
| Mmt | D-Arg | Phe | Dab | | $NH_2$ |
| Mmt | D-Arg | Phe | Dap | | $NH_2$ |
| Tmt | D-Arg | Phe | Lys | | $NH_2$ |
| Tmt | D-Arg | Phe | Orn | | $NH_2$ |
| Tmt | D-Arg | Phe | Dab | | $NH_2$ |
| Tmt | D-Arg | Phe | Dap | | $NH_2$ |
| Hmt | D-Arg | Phe | Lys | | $NH_2$ |
| Hmt | D-Arg | Phe | Orn | | $NH_2$ |
| Hmt | D-Arg | Phe | Dab | | $NH_2$ |
| Hmt | D-Arg | Phe | Dap | | $NH_2$ |
| Mmt | D-Lys | Phe | Lys | | $NH_2$ |
| Mmt | D-Lys | Phe | Orn | | $NH_2$ |
| Mmt | D-Lys | Phe | Dab | | $NH_2$ |
| Mmt | D-Lys | Phe | Dap | | $NH_2$ |
| Mmt | D-Lys | Phe | Arg | | $NH_2$ |
| Tmt | D-Lys | Phe | Lys | | $NH_2$ |
| Tmt | D-Lys | Phe | Orn | | $NH_2$ |
| Tmt | D-Lys | Phe | Dab | | $NH_2$ |
| Tmt | D-Lys | Phe | Dap | | $NH_2$ |
| Tmt | D-Lys | Phe | Arg | | $NH_2$ |
| Hmt | D-Lys | Phe | Lys | | $NH_2$ |
| Hmt | D-Lys | Phe | Orn | | $NH_2$ |
| Hmt | D-Lys | Phe | Dab | | $NH_2$ |
| Hmt | D-Lys | Phe | Dap | | $NH_2$ |
| Hmt | D-Lys | Phe | Arg | | $NH_2$ |
| Mmt | D-Lys | Phe | Arg | | $NH_2$ |
| Mmt | D-Orn | Phe | Arg | | $NH_2$ |
| Mmt | D-Dab | Phe | Arg | | $NH_2$ |
| Mmt | D-Dap | Phe | Arg | | $NH_2$ |
| Mmt | D-Arg | Phe | Arg | | $NH_2$ |
| Tmt | D-Lys | Phe | Arg | | $NH_2$ |
| Tmt | D-Orn | Phe | Arg | | $NH_2$ |
| Tmt | D-Dab | Phe | Arg | | $NH_2$ |
| Tmt | D-Dap | Phe | Arg | | $NH_2$ |
| Tmt | D-Arg | Phe | Arg | | $NH_2$ |
| Hmt | D-Lys | Phe | Arg | | $NH_2$ |
| Hmt | D-Orn | Phe | Arg | | $NH_2$ |
| Hmt | D-Dab | Phe | Arg | | $NH_2$ |
| Hmt | D-Dap | Phe | Arg | | $NH_2$ |
| Hmt | D-Arg | Phe | Arg | | $NH_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of analogs useful in the practice of the present invention that do not activate mu-opioid receptors include, but are not limited to, the aromatic-cationic peptides shown in Table 6.

TABLE 6

Peptide Analogs Lacking Mu-Opioid Activity

| Amino Acid Position 1 | Amino Acid Position 2 | Amino Acid Position 3 | Amino Acid Position 4 | Amino Acid Position 5 | Amino Acid Position 6 | Amino Acid Position 7 | C-Terminal Modification |
|---|---|---|---|---|---|---|---|
| D-Arg | Dmt | Lys | Phe | | | | $NH_2$ |
| D-Arg | Dmt | Phe | Lys | | | | $NH_2$ |
| D-Arg | Phe | Lys | Dmt | | | | $NH_2$ |
| D-Arg | Phe | Dmt | Lys | | | | $NH_2$ |
| D-Arg | Lys | Dmt | Phe | | | | $NH_2$ |
| D-Arg | Lys | Phe | Dmt | | | | $NH_2$ |
| Phe | Lys | Dmt | D-Arg | | | | $NH_2$ |
| Phe | Lys | D-Arg | Dmt | | | | $NH_2$ |
| Phe | D-Arg | Phe | Lys | | | | $NH_2$ |
| Phe | D-Arg | Dmt | Lys | | | | $NH_2$ |
| Phe | D-Arg | Lys | Dmt | | | | $NH_2$ |
| Phe | Dmt | D-Arg | Lys | | | | $NH_2$ |
| Phe | Dmt | Lys | D-Arg | | | | $NH_2$ |
| Lys | Phe | D-Arg | Dmt | | | | $NH_2$ |
| Lys | Phe | Dmt | D-Arg | | | | $NH_2$ |
| Lys | Dmt | D-Arg | Phe | | | | $NH_2$ |
| Lys | Dmt | Phe | D-Arg | | | | $NH_2$ |
| Lys | D-Arg | Phe | Dmt | | | | $NH_2$ |
| Lys | D-Arg | Dmt | Phe | | | | $NH_2$ |
| D-Arg | Dmt | D-Arg | Phe | | | | $NH_2$ |
| D-Arg | Dmt | D-Arg | Dmt | | | | $NH_2$ |
| D-Arg | Dmt | D-Arg | Tyr | | | | $NH_2$ |
| D-Arg | Dmt | D-Arg | Trp | | | | $NH_2$ |
| Trp | D-Arg | Phe | Lys | | | | $NH_2$ |
| Trp | D-Arg | Tyr | Lys | | | | $NH_2$ |
| Trp | D-Arg | Trp | Lys | | | | $NH_2$ |
| Trp | D-Arg | Dmt | Lys | | | | $NH_2$ |
| D-Arg | Trp | Lys | Phe | | | | $NH_2$ |
| D-Arg | Trp | Phe | Lys | | | | $NH_2$ |
| D-Arg | Trp | Lys | Dmt | | | | $NH_2$ |
| D-Arg | Trp | Dmt | Lys | | | | $NH_2$ |
| D-Arg | Lys | Trp | Phe | | | | $NH_2$ |
| D-Arg | Lys | Trp | Dmt | | | | $NH_2$ |
| Cha | D-Arg | Phe | Lys | | | | $NH_2$ |
| Ala | D-Arg | Phe | Lys | | | | $NH_2$ |

Cha = cyclohexyl

The amino acids of the peptides shown in Table 5 and 6 may be in either the L-or the D-configuration.

Synthesis of the Peptides

The peptides useful in the methods of the present invention may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol.* 289, Academic Press, Inc, New York (1997).

Prophylactic and Therapeutic Uses of Aromatic-Cationic Peptides.

General. The aromatic-cationic peptides of the present invention are useful to prevent or treat disease. Specifically, the invention provides for both prophylactic and therapeutic methods of treating a subject at risk of (or susceptible to) a disorder or having a disorder associated with insulin resistance. Insulin resistance is generally associated with type II diabetes, coronary artery disease, renal dysfunction, atherosclerosis, obesity, hyperlipidemia, and essential hypertension. Insulin resistance is also associated with fatty liver, which can progress to chronic inflammation (NASH; "non-alcoholic steatohepatitis"), fibrosis, and cirrhosis. Cumulatively, insulin resistance syndromes, including, but not limited to diabetes, underlie many of the major causes of morbidity and death of people over age 40. Accordingly, the present invention provides methods for the prevention and/or treatment of insulin resistance and associated syndromes in a subject comprising administering an effective amount of an aromatic-cationic peptide to a subject in need thereof. For example, a subject can be administered an aromatic-cationic peptide compositions of the present invention in an effort to improve the sensitivity of mammalian skeletal muscle tissues to insulin. In one embodiment, the aromatic-cationic peptides of the invention are useful to prevent drug-induced obesity, insulin resistance, and/or diabetes, when the peptide is administered with a drug that shows a side-effect of causing one or more of these conditions (e.g., olanzapine, Zyprexa®).

Determination of the Biological Effect of the Aromatic-Cationic Peptide-Based Therapeutic. In various embodiments of the invention, suitable in vitro or in vivo assays are performed to determine the effect of a specific aromatic-cationic peptide-based therapeutic and whether its administration is indicated for treatment of the affected tissue in a subject. In various embodiments, in vitro assays can be performed with representative cells of the type(s) involved in the subject's disorder, to determine if a given aromatic-cationic peptide-based therapeutic exerts the desired effect upon the cell type(s). Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects. Increased or decreased insulin resistance or sensitivity can be readily detected by quantifying body weight, fasting glucose/insulin/free fatty acid, glucose tolerance (OGTT), in vitro muscle insulin sensitivity, markers of insulin signaling (e.g., Akt-P, IRS-P), mitochondrial function (e.g., respiration or $H_2O_2$ emission), markers of intracellular oxidative stress (e.g., lipid peroxidation, GSH/GSSG ratio or aconitase activity) or mitochondrial enzyme activity.

Prophylactic Methods. In one aspect, the invention provides a method for preventing, in a subject, a disease or condition associated with insulin resistance in skeletal muscle tissues, by administering to the subject an aromatic-cationic peptide that modulates one or more signs or markers of insulin resistance, e.g., body weight, fasting glucose/insulin/free fatty acid, glucose tolerance (OGTT), in vitro muscle insulin sensitivity, markers of insulin signaling (e.g., Akt-P, IRS-P), mitochondrial function (e.g., respiration or $H_2O_2$ emission), markers of intracellular oxidative stress (e.g., lipid peroxidation, GSH/GSSG ratio or aconitase activity) or mitochondrial enzyme activity.

Subjects at risk for a disease that is caused or contributed to by aberrant mitochondrial function or insulin resistance can be identified by, e.g., any or a combination of diagnostic or prognostic assays as described herein. In prophylactic applications, pharmaceutical compositions or medicaments of aromatic-cationic peptides are administered to a subject susceptible to, or otherwise at risk of a disease or condition in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. Administration of a prophylactic aromatic-cationic can occur prior to the manifestation of symptoms characteristic of the aberrancy, such that a disease or disorder is prevented or, alternatively, delayed in its progression. Depending upon the type of aberrancy, e.g., a aromatic-cationic peptide which acts to enhance or improve mitochondrial function can be used for treating the subject. The appropriate compound can be determined based on screening assays described herein.

Therapeutic Methods. Another aspect of the invention includes methods of modulating insulin resistance or sensitivity in a subject for therapeutic purposes. In therapeutic applications, compositions or medicaments are administered to a subject suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically-or prophylactically-effective dose. These modulatory methods can be performed in vitro (e.g., by culturing the cell with the aromatic-cationic peptide) or, alternatively, in vivo (e.g., by administering the aromatic-cationic peptide to a subject). As such, the invention provides methods of treating an individual afflicted with a insulin resistance-associated disease or disorder.

Modes of Administration and Effective Dosages

Any method known to those in the art for contacting a cell, organ or tissue with a peptide may be employed. Suitable methods include in vitro, ex vivo, or in vivo methods. In vivo methods typically include the administration of an aromatic-cationic peptide, such as those described above, to a mammal, preferably a human. When used in vivo for therapy, the aromatic-cationic peptides of the present invention are administered to the subject in effective amounts (i.e., amounts that have desired therapeutic effect). They will normally be administered parenterally or orally. The dose and dosage regimen will depend upon the degree of the insulin resistance-related disease or disorder, the characteristics of the particular aromatic-cationic peptide used, e.g., its therapeutic index, the subject, and the subject's history.

The effective amount may be determined during pre-clinical trials and clinical trials by methods familiar to physicians and clinicians. An effective amount of a peptide useful in the methods of the present invention, preferably in a pharmaceutical composition, may be administered to a mammal in need thereof by any of a number of well-known methods for administering pharmaceutical compounds. The peptide may be administered systemically or locally.

The aromatic-cationic peptides described herein can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g. vials of drug, vials of diluent, syringes and needles) for a treatment course (e.g. 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The aromatic-cationic peptide compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed my iontophoresis.

A therapeutic protein or peptide can be formulated in a carrier system. The carrier can be a colloidal system. The colloidal system can be a liposome, a phospholipid bilayer vehicle. In one embodiment, the therapeutic protein is encapsulated in a liposome while maintaining protein integrity. As one skilled in the art would appreciate, there are a variety of methods to prepare liposomes. (See Lichtenberg et al., *Methods Biochem. Anal.*, 33:337-462 (1988); Anselem et al., *Liposome Technology*, CRC Press (1993)). Liposomal formulations can delay clearance and increase cellular uptake (See Reddy, *Ann. Pharmacother.*, 34 (7-8):915-923 (2000)).

The carrier can also be a polymer, e.g., a biodegradable, biocompatible polymer matrix. In one embodiment, the therapeutic protein can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34 (7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods* 4 (3) 201-9 (1994); and Gregoriadis, "Engineering Liposomes for Drug Delivery: Progress and Problems," *Trends Biotechnol.* 13 (12):527-37 (1995). Mizguchi et al., *Cancer Lett.* 100:63-69 (1996), describes the use of fusogenic liposomes to deliver a protein to cells both in vivo and in vitro.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the aromatic-cationic peptides of the present invention, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.1-10,000 micrograms per kg body weight. In one embodiment, aromatic-cationic peptide concentrations in a carrier range from 0.2 to 2000 micrograms per delivered milliliter. An exemplary treatment regime entails administration once per day or once a week. Intervals can also be irregular as indicated by measuring blood levels of glucose or insulin in the subject and adjusting dosage or administration accordingly. In some methods, dosage is adjusted to achieve a desired fasting glucose or fasting insulin concentration. In therapeutic applications, a relatively high dosage at relatively short intervals is sometimes required until progression of the disease is reduced or terminated, and preferably until the subject shows partial or complete amelioration of symptoms of disease. Thereafter, the patient can be administered a prophylactic regime.

In some embodiments, a therapeutically effective amount of an aromatic-cationic peptide may be defined as a concentration of peptide at the target tissue of $10^{-11}$ to $10^{-6}$ molar, e.g., approximately $10^{-7}$ molar. This concentration may be delivered by systemic doses of 0.01 to 100 mg/kg or equivalent dose by body surface area. The schedule of doses would be optimized to maintain the therapeutic concentration at the target tissue, most preferably by single daily or weekly administration, but also including continuous administration (e.g. parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the invention can be any mammal, including, for example, farm animals, such as sheep, pigs, cows, and horses; pet animals, such as dogs and cats; laboratory animals, such as rats, mice and rabbits. In a preferred embodiment, the mammal is a human.

Labeled Aromatic-Cationic Peptides and Diagnostic Methods

Disclosed herein are methods comprising providing a labeled aromatic-cationic peptide to a cell or a subject, wherein the peptide has a detectable label conjugated to a peptide. In one embodiment, a specific combination of a particular label with a particular peptide allows for detecting localization of the peptide within a cell.

Labeled Aromatic Cationic Peptides. In one embodiment, the aromatic-cationic peptides of the present invention are coupled with a label moiety, i.e., detectable group. The particular label or detectable group conjugated to the aromatic-cationic peptide of the invention is not a critical aspect of the invention, so long as it does not significantly interfere with the specific activity of the aromatic cationic peptide of the present invention. The detectable group can be any material having a detectable physical or chemical property. Such detectable labels have been well-developed in the field of immunoassays and imaging, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^3$H, $^{14}$C, $^{35}$S, $^{125}$I, $^{121}$I, $^{112}$In, $^{99m}$Tc), other imaging agents such as microbubbles (for ultrasound imaging), $^{18}$F, $^{11}$C, $^{15}$O, (for Positron emission tomography), $^{99m}$TC, $^{111}$In (for Single photon emission tomography), enzymes (e.g., horse radish peroxidase, alkaline phosphatase and others commonly used in an ELISA), and calorimetric labels such as colloidal gold or colored glass or plastic (e.g., polystyrene, polypropylene, latex, and the like) beads. Patents that described the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also Handbook of Fluorescent Probes and Research Chemicals (6$^{th}$ Ed., Molecular Probes, Inc., Eugene Oreg.).

The label can be coupled directly or indirectly to the desired component of an assay according to methods well known in the art. As indicated above, a wide variety of labels can be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, e.g., biotin, thyroxine, and cortisol, it can be used in conjunction with the labeled, naturally-occurring anti-ligands.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds useful as labeling moieties, include, but are not limited to, e.g., fluorescein and its derivatives, rhodamine and its derivatives, dansyl, umbelliferone, and the like. Chemiluminescent compounds useful as labelling moieties, include, but are not limited to, e.g., luciferin, and 2,3-dihydrophthalazinediones, e.g., luminol. For a review of various labeling or signal-producing systems which can be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally simple colorimetric labels can be detected simply by observing the color associated with the label. Thus, in various dipstick assays, conjugated gold often appears pink, while various conjugated beads appear the color of the bead.

Diagnostic Applications of Labeled Aromatic Cationic Peptides

In one embodiment, the method comprising administering the labeled aromatic-cationic peptide to a cell or a subject and achieving a desired localization. In one embodiment of the invention, the method comprising administering the labeled aromatic-cationic peptide to a human cell and achieving a desired localization. A desired localization refers to a labeled aromatic-cationic peptide being specifically sequestered in a desired cellular component, e.g., the mitochondrion. Those skilled in the art will recognize that any number of labeled aromatic-cationic peptides of the present invention may be delivered to a cell and the method remains within the spirit and scope of the present invention. In addition, those skilled in the art will recognize that cellular imaging various types of cells from various types of sources are within the spirit and scope of the present invention.

Labeled aromatic-cationic peptides of the invention can be used in vitro and/or in vivo to detect target molecules of interest. In many cases, the labeled aromatic-cationic peptides can simply be added to test samples in a homogenous assay, not requiring addition of multiple reagents and/or wash steps before detection of the target. Labeled aromatic-cationic peptides of the invention may contact target molecules or cellular compartments in vitro by simple addition to a test sample containing the target molecules or cells. Test samples for in vitro assays can be, e.g., molecular libraries, cell lysates, analyte eluates from chromatographic columns, and the like. The in vitro assay often takes place in a chamber, such as, e.g., a well of a multiwell plate, a test tube, an Eppendorf tube, a spectrophotometer cell, conduit of an analytical system, channels of a microfluidic system, an open array, and the like.

Where labeled aromatic-cationic peptides of the invention are administered to living cells, binding can take place with targets on the cell surface or within the cell itself, e.g., the labeled aromatic-cationic peptide is transferred into the cell to make contact with an intracellular target molecule. In some cases, the labeled aromatic-cationic peptide can penetrate a cell suspected of containing a selected target passively by mere exposure of the cell to a medium containing the labeled aromatic-cationic peptides. In other embodiments, the labeled aromatic-cationic peptide is actively transferred into the cell by mechanisms known in the art, such as, e.g., poration, injection, transduction along with transfer peptides, and the like.

Following contact of the cells with the labeled aromatic-cationic peptides, the methods may comprise irradiating the cell with an energy source. In one embodiment, the energy source is a light source. In one embodiment, the imaging agent of the labeled aromatic-cationic peptide is activated by the energy source. In one embodiment, the imaging agent of the labeled aromatic-cationic peptide gives off a detectable signal when it is illuminated by the energy source. In one embodiment of the invention, the imaging agent gives off a detectable fluorescence in response to the energy source.

In one embodiment of the invention, the fluorescence given off by the imaging agent in response to the light source may be observed and measured. In one embodiment of the invention, the fluorescence is observed and measured with a confocal microscope. Those skilled in the art will recognize that various devices used to observe and measure fluorescence are within the spirit and scope of the present invention.

EXAMPLES

The present invention is further illustrated by the following examples, which should not be construed as limiting in any way.

Example 1

Mitochondrial Dysfunction in Rats Fed a High Fat Diet

To determine the potential impact of diet-induced obesity on the control of cellular redox balance in skeletal muscle, a novel approach to measure the rate of mitochondrial $H_2O_2$ emission in permeabilized skeletal muscle fiber bundles was developed. See Anderson et al., *J. Clin Invest* (doi: 10.1172/JCI37048). During basal (state 4) respiration supported by NADH-linked complex I substrates, the rate of superoxide formation is low, representing 0.1-0.5% of total $O_2$ utilization (Anderson & Neufer, *Am J Physiol Cell Physiol* 290, C844-851 (2006); St-Pierre et al., *J Biol Chem* 277, 44784-44790 (2002)). However, respiration supported exclusively by succinate, an $FADH_2$-linked complex II substrate, elicits high rates of superoxide production by generating reverse electron flow back into complex I (Anderson & Neufer, *Am J Physiol Cell Physiol* 290, C844-851 (2006); St-Pierre et al., *J Biol Chem* 277, 44784-44790 (2002); Liu et al., *J Neurochem* 80, 780-787 (2002); Turrens et al., *Biochem J* 191, 421-427 (1980)). This Example describes methods for measuring mitochondrial function in permeabilized muscle tissues and examines the effects of a high fat diet on mitochondrial function.

Animals and reagents. Thirty male Sprague-Dawley rats were obtained from Charles River Laboratory (Wilmington, Mass.) and housed in a temperature (22° C.) and light-controlled room and given free access to food and water. Twenty of the original thirty rats were kept on a high (60%) fat diet (Research Dyets, Bethlehem, Pa.). Skeletal muscle was obtained from anesthetized animals (100 mg/kg ip ketamine-xylazine). After surgery, animals were killed by cervical dislocation while anesthetized. Amplex Red Ultra reagent was obtained from Molecular Probes (Eugene, Oreg.). Stigmatellin and horseradish peroxidase (HRP) were obtained from Fluka Biochemika (Buchs, Switzerland), and all other chemicals were purchased from Sigma-Aldrich (St. Louis, Mo.). All animal studies were approved by the East Carolina University Institutional Animal Care and Use Committee.

Preparation of permeabilized muscle fiber bundles. Briefly, small portions (25 mg) of soleus, RG, and WG muscle were dissected and placed in ice-cold buffer X, containing 60 mM K-MES, 35 mM KCl, 7.23 mM $K_2$ EGTA, 2.77 mM $CaK_2$EGTA, 20 mM imidazole, 0.5 mM DTT, 20 mM taurine, 5.7 mM ATP, 15 mM PCr, and 6.56 mM $MgCl_2 \cdot 6H_2O$ (pH 7.1, 295 mosmol/kg $H_2O$). The muscle was trimmed of connective tissue and cut down to fiber bundles (2×7 mm, 4-8 mg wet wt). With a pair of needle-tipped forceps under a dissecting microscope, fibers were gently separated from one another to maximize surface area of the fiber bundle, leaving only small regions of contact. To permeabilize the myofibers, each fiber bundle was placed in ice-cold buffer X containing 50 µg/ml saponin and incubated on a rotator for 30 min at 4° C. Following permeabilization, the permeabilized fiber bundles (PmFBs) were washed in ice-cold Buffer Z containing (in mM) 110 K-MES, 35 KCl, 1 EGTA, 10 $K_2HPO_4$, 3 $MgCl_2-6H_2O$, 5 mg/ml BSA, 0.1 glutamate and 0.05 malate (pH 7.4, 295 mOsm) and remained in Buffer Z on a rotator at 4° C. until analysis (<2 h).

Mitochondrial respiration and $H_2O_2$ emission measurements. High resolution respirometric measurements were conducted at 30° C. in Buffer Z using the Oroboros $O_2K$ Oxygraph (Innsbruck, Austria). Mitochondrial $H_2O_2$ emission was measured at 30° C. during state 4 respiration in Buffer Z (10 µg/ml oligomycin) by continuously monitoring oxidation of Amplex Red using a Spex Fluoromax 3 (Jobin Yvon, Ltd.) spectrofluorometer with temperature control and magnetic stirring at >1000 rpm. Amplex Red reagent reacts with $H_2O_2$ in a 1:1 stoichiometry catalyzed by HRP to yield the fluorescent compound resorufin and molar equivalent $O_2$. Resorufin has excitation/emission characteristics of 563 nm/587 nm and is extremely stable once formed. After baseline fluorescence (reactants only) was established, the reaction was initiated by addition of a permeabilized fiber bundle to 300 µl of buffer Z containing 5 µM Amplex Red and 0.5 U/ml HRP, with succinate at 37° C. For the succinate experiments, the fiber bundle was washed briefly in buffer Z without substrate to eliminate residual pyruvate and malate from the wash. Where stated, 10 µg/ml oligomycin was included in the reaction buffer to block ATP synthase and ensure state 4 respiration. At the conclusion of each experiment, PmFBs were washed in $ddH_2O$ to remove salts and freeze-dried in a lyophilizer (LabConco). The rate of respiration is expressed as $pmol \cdot s^{-1} \cdot mg$ dry $weight^{-1}$, and mitochondrial $H_2O_2$ emission expressed as $pmol \cdot min^{-1} \cdot mg$ dry $weight^{-1}$.

Statistical analyses. Data are presented as means±SE. Statistical analyses were performed using a one-way ANOVA with Student-Newman-Keuls method for analysis of significance among groups. The level of significance was set at P<0.05.

Results. To provide a better measure of the respiratory system's potential to generate and/or emit $H_2O_2$ in relation to progressively increasing metabolic flux (without a change in ATP demand), the changes in $H_2O_2$ emission in response to titration of succinate during state 4 respiration supported by the complex I substrates pyruvate and malate were continuously monitored. By plotting the rate of $H_2O_2$ emission versus succinate concentration, it was reasoned that a leftward shift in the curve would indicate an increase, whereas a rightward shift would indicate a decrease, in the oxidant emitting potential of the respiratory system. FIG. 1A shows a representative trace comparing rates of mitochondrial $H_2O_2$ emission from permeabilized skeletal muscle fibers prepared from rats fed standard chow, lard 3 days or high fat chow 3 weeks. The experiment is started by addition of a small amount of glutamate and malate (G/M) to a de-energized fiber bundle (FB), and followed by successively increasing concentrations (in mM) of succinate.

Figure 1B:
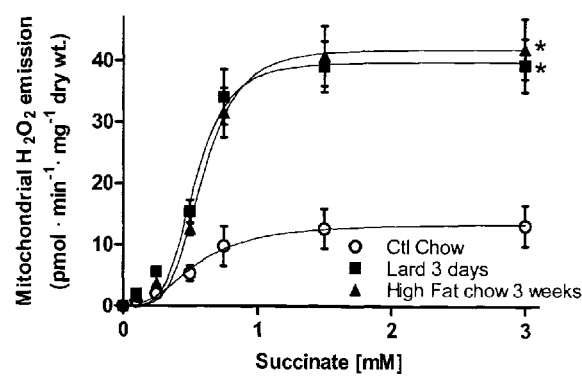
Figure 2:
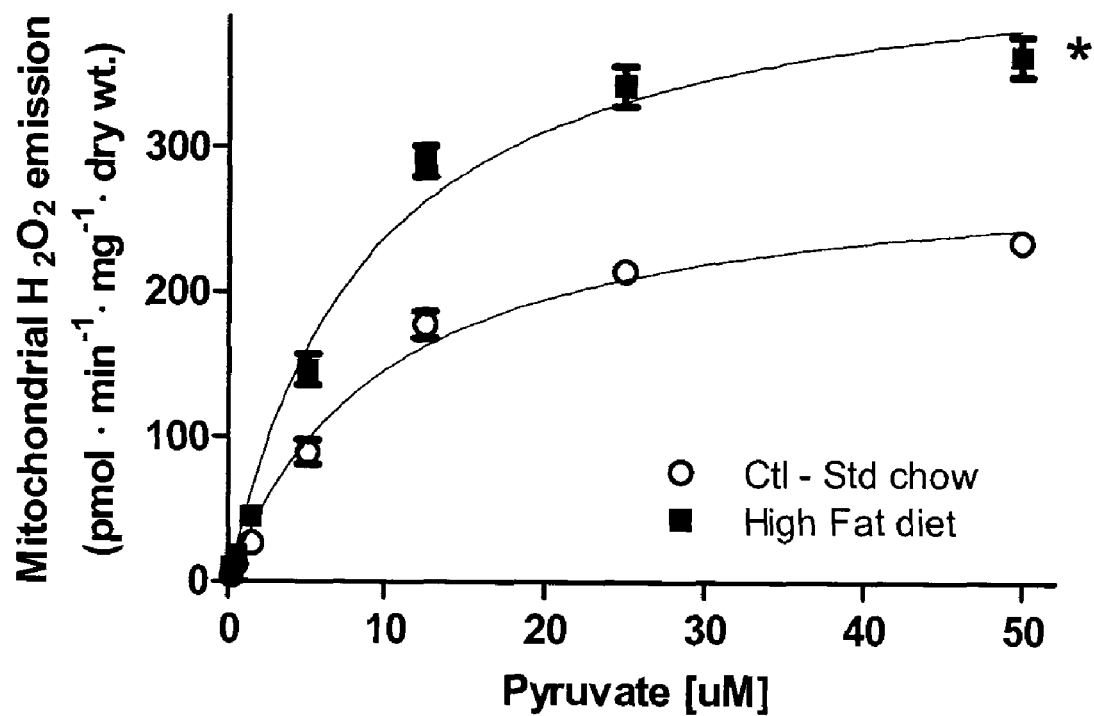
FIG. 2 is a chart showing mitochondrial $H_2O_2$ emission in the presence of antimycin A in skeletal muscle fibers prepared from high fat fed rats compared to control chow. Mitochondrial $H_2O_2$ emission in the presence of antimycin A was measured in both groups with a titration of pyruvate and malate.

Surprisingly, switching rats from a standard high carbohydrate chow diet to 100% fat (lard) for 3 days or a 60% high fat diet for 3 weeks induced a remarkable 3 to 4-fold increase in the maximal rate of mitochondrial $H_2O_2$ emission with little to no change in sensitivity (FIGS. 1A and 1B). Addition of rotenone at the conclusion of succinate titration eliminated $H_2O_2$ emission (not shown), confirming complex I as the source of superoxide production from both control and high fat fed rats. Mitochondrial oxidant emitting potential was also measured by titrating pyruvate/malate in the presence of antimycin (complex III inhibitor), again revealing >2-fold higher maximal rate of $H_2O_2$ emission in high fat fed rats (FIG. 2). These findings demonstrate that the mitochondrial oxidant emitting potential in skeletal muscle is markedly increased within as little as three days after transitioning to a high fat diet.

Example 2

Effects of Aromatic-Cationic Peptides on ROS Production in Rats Fed a High Fat Diet Superoxide production is higher during basal respiration supported by fatty acid versus carbohydrate metabolism, raising the possibility that the increase in mitochondrial oxidant emitting potential induced by a high fat diet may be precipitated by a persistent elevation in oxidant production (i.e., by a ROS-induced ROS release mechanism). To test this hypothesis, the effects of the aromatic-cationic peptide SS-31 on mitochondrial function in high fat fed rats were examined. SS-31 is unique in that it localizes specifically within the mitochondrial inner membrane where it scavenges ROS without affecting membrane potential or respiratory control. This small peptide antioxidant has been shown to effectively reduce ROS in hearts subjected to myocardial stunning (Zhao et al., *J Biol Chem* 279, 34682-34690 (2004)), in pancreatic islet cells after transplantation (Thomas et al., *Journal of the American Society of Nephrology* 16, TH-FC067 (2005)), and in animal models of Parkinson's and amyotrophic lateral sclerosis disease (Petri et al., *J Neurochem* 98, 1141-1148 (2006); Szeto et al., *AAPS J* 8, E521-531 (2006)).

Figure 3A:
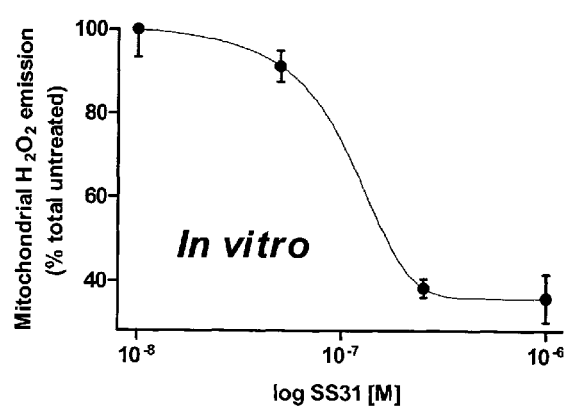
FIGS. 3A-H are a series of charts showing the effect of the SS-31 peptide of the invention on the oxidation state of muscle tissues. Subjects include rats fed a normal diet (Ctl), a high fat diet (HF), or a high fat diet with daily SS-31 administration (HF+SS-31).
Figure 3B:
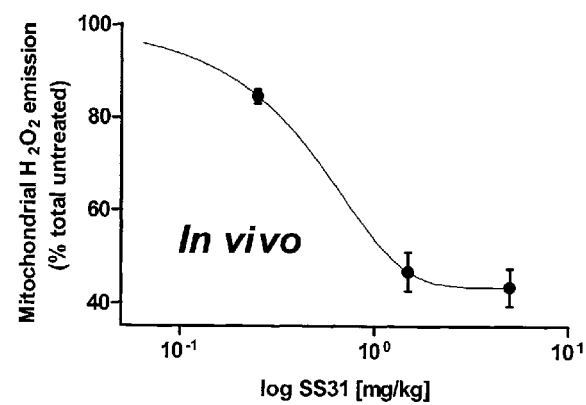

Ten rats of the high fat fed group received daily intraperitoneal injections of SS-31 dissolved in phosphate-buffered saline (1.5 mg/kg). Dose response curves for SS-31 were established in vitro (FIG. 3A) and in vivo (FIG. 3B). Mitochondrial function was measured according to the methods described in Example 1. Both dose response curves revealed greater than 50% reduction in mitochondrial $H_2O_2$ emission during succinate-supported respiration.

Figure 3C:
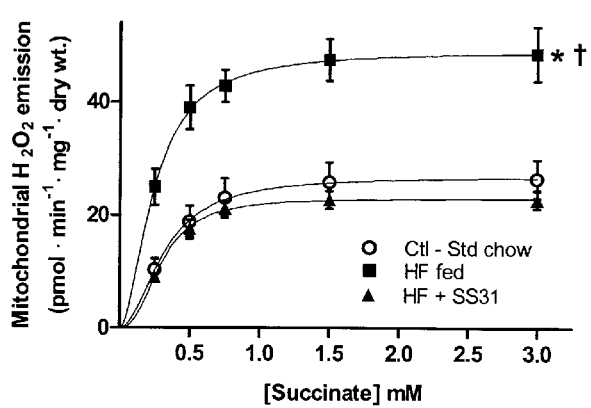
Figure 3D:
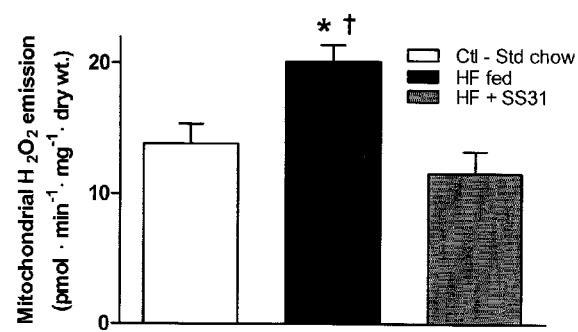
Figure 3E:
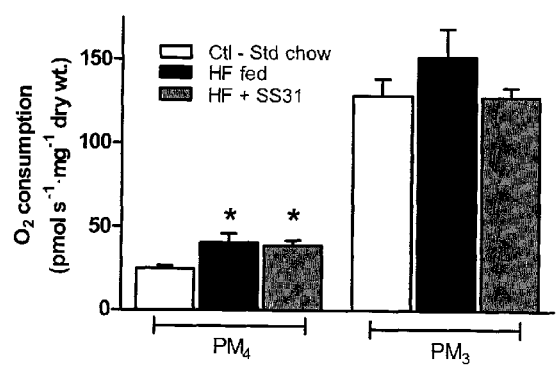
Figure 3F:
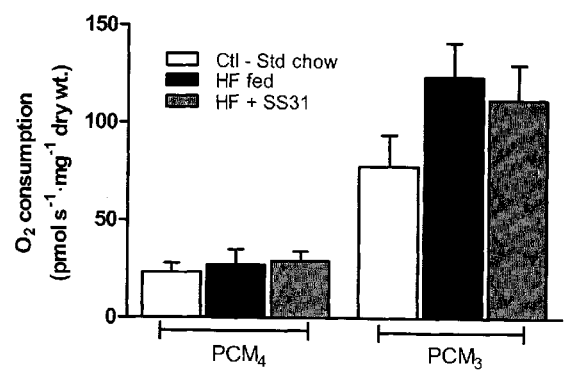

Next, rats were placed on a high fat diet (60%) for six weeks with or without daily administration of SS-31. Succinate titration experiments conducted on permeabilized fibers again revealed a remarkable 3-fold increase in the maximal rate of $H_2O_2$ emission in high fat fed rats (FIG. 3C). Permeabilized fibers from high fat fed rats also generated nearly a 2-fold greater rate of $H_2O_2$ emission during basal respiration supported by palmitoyl-carnitine (FIG. 3D). However, in high fat fed rats treated with SS-31, the increase in mitochondrial oxidant emitting potential during both succinate and palmitoyl-carnitine supported respiration was completely prevented (FIGS. 3C & 3D). Basal respiration supported by pyruvate/malate was slightly increased in fibers from high fat fed rats, suggesting some degree of uncoupling (FIG. 3E). However, in high fat fed rats, basal rates of pyruvate/malate- or palmitoyl-carnitine-supported respiration were not affected by SS-31 treatment (FIGS. 3E and 3F), indicating that the normalization of $H_2O_2$ emission with SS-31 treatment was not mediated by an increase in proton leak. SS-31 treatment also did not affect the weight gain in high fat fed rats (data not shown). Collectively, these findings demonstrate that administration of a mitochondrial targeted antioxidant, such as the aromatic-cationic peptides of the invention, is sufficient to prevent or compensate for the increase in mitochondrial oxidant emitting potential induced by a high fat diet. As such, administration of the aromatic-cationic peptides of the present invention is useful in methods of preventing or treating insulin resistance caused by mitochondrial dysfunction in mammalian subjects.

It is increasingly recognized that the intracellular localization and activity of many proteins (e.g., receptors, kinases/phosphatases, transcription factors, etc.) is reversibly controlled by the oxidation state of specific thiol (—SH)-containing residues, leading to the concept that shifts in the intracellular redox environment affect the overall biological status of the cell (Schafer and Buetner, *Free Radic Biol Med* 30, 1191-1212 (2001)). Glutathione (GSH), the most abundant redox buffer in cells, is reversibly oxidized to GSSG by glutathione peroxidase in the presence of $H_2O_2$, and reduced back to GSH by glutathione reductase with electrons donated by NADPH. The ratio of GSH/GSSG is very dynamic, largely reflecting the overall redox environment of the cell.

Protein homogenates were prepared by homogenizing 100 mg of powered frozen muscle in a buffer containing in mM: 10 Tris, 1 EDTA, 1 EGTA, 2 NaOrthovanadate, 2 NaPyrophosphate, 5 NaF, protease inhibitor cocktail (Complete) at pH 7.2. After homogenization, 1% Triton X-100 was added to the protein suspension, cotexed and allowed to sit on ice for 5 minutes. The tubes were then spun at 10,000 rpm for 10 minutes to pellet the insoluble debris. For GSSG measurement, tissue was homogenized in a solution containing 20 mM Methyl-2-vinylpyridinium triflate to scavenge all reduced thiols in the sample. Total GSH and GSSG were then measured using the reagents and calibration set provided by the GSH/GSSG assay (Oxis Research) according to the manufacturer's instructions, with small modifications as needed.

Figure 3G:
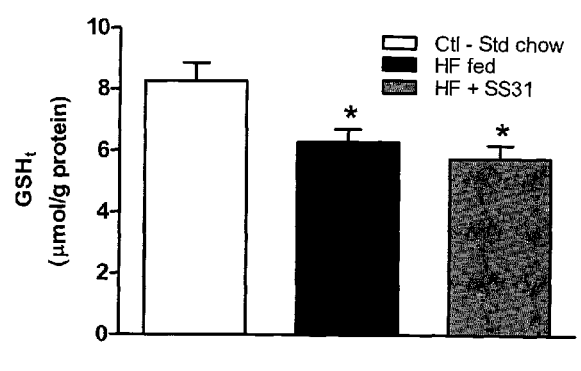
Figure 3H:
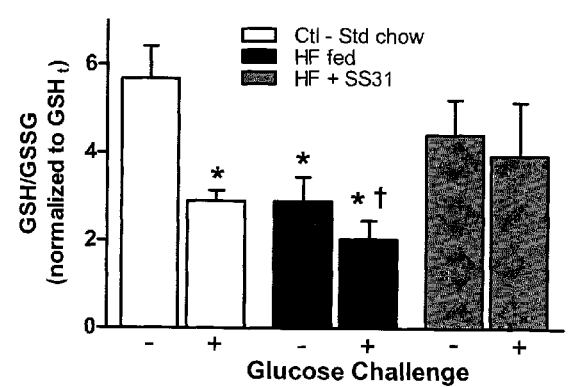

Surprisingly, it was found that high fat feeding resulted in an ~30% reduction in total cellular glutathione content (GSHT) irrespective of SS-31 treatment (FIG. 3G), demonstrating that high fat intake compromises GSH-mediated redox buffering capacity in skeletal muscle. To establish a link between the increased mitochondrial oxidant emission brought about by high fat diet and its effect on overall redox environment of skeletal muscle, both GSH and GSSG were measured in skeletal muscle of chow fed and high fat fed rats under two conditions; after a 10 h fast and 1 h after administration of a standard glucose load (oral gavage, 10 h fasted). In chow fed controls, glucose ingestion elicited an 50% reduction in the GSH/GSSG ratio (normalized to GSHT, FIG. 3H), presumably reflecting an acute shift to a more oxidized state in response to the increase in insulin-stimulated glucose metabolism. In high fat fed rats, the GSH/GSSG ratio was already reduced by 50% in the h fasted state relative to chow fed controls and declined further in response to the glucose ingestion. SS-31 treatment, however, preserved the GSH/GSSG ratio near control levels, even in response to glucose ingestion. These findings demonstrate that a high fat diet shifts the intracellular redox environment in skeletal muscle to a more oxidized state. Treatment with SS-31 was able to preserve the intracellular redox state in skeletal muscle, presumably by scavenging primary oxidants and thereby compensating for the reduction in total GSH-mediated redox buffering capacity induced by a high fat diet. Thus, administration of a mitochondrial-targeted antioxidant, such as the aromatic-cationic peptides of the invention, either prevents or compensates for the metabolic dysfunction that develops in rats fed a high fat diet. As such, administration of the aromatic-cationic peptides of the present invention is useful in methods of preventing or treating this metabolic dysfunction in mammalian subjects.

Example 3

Oral Glucose Tolerance Tests

To determine whether mitochondrial-derived changes in intracellular redox environment may be linked to the etiology of high fat diet-induced insulin resistance, oral glucose tolerance tests were performed in rats after the six week high fat diet. On the day of experiments, food was removed 10 hr prior to administration of a 2 g/kg glucose solution via gavage. Glucose levels were determined on whole blood samples (Lifescan, Milpitas, Calif.). Serum insulin levels were determined via a rat/mouse ELISA kit (Linco Research, St. Charles, Mo.). Fasting data were used to determine homeostatic model assessment (HOMA)-calculated as fasting insulin (μU/ml) x fasting glucose (mM)/22.5.

Figure 4A:
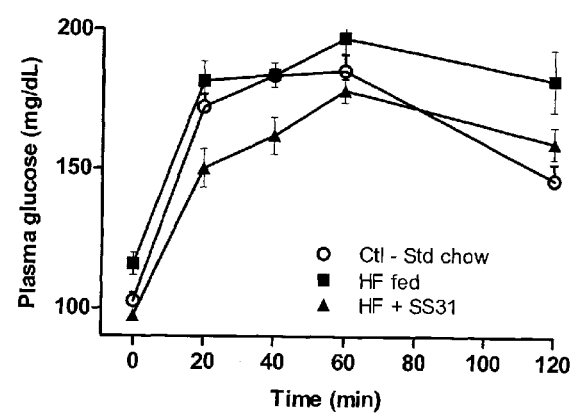
FIGS. 4A-E are a series of charts showing the effect of the SS-31 peptide of the invention on the insulin resistance in muscle tissues.
Figure 4B:
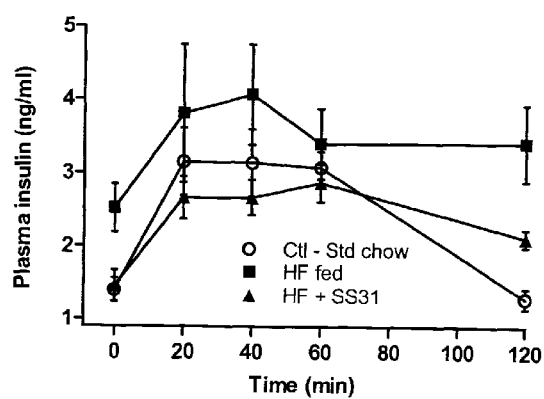

Blood glucose (FIG. 4A) and insulin (FIG. 4B) responses to the oral glucose challenge were higher and more sustained in high fat fed rats compared with standard chow-fed rats. Treatment of high fat fed rats with SS-31 normalized both the blood glucose and insulin responses to the oral glucose challenge.

Figure 4C:
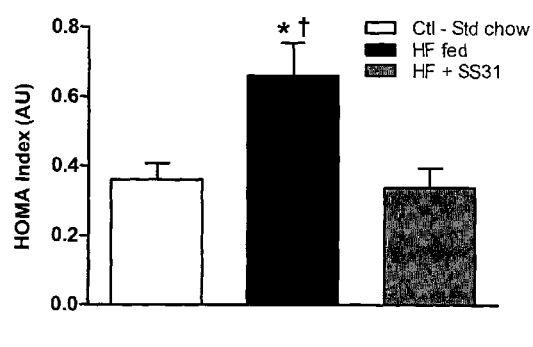
Figure 4D:
Figure 4E:
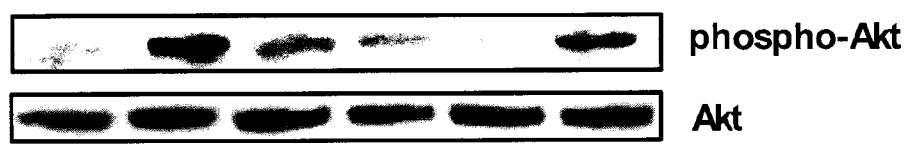
Figure 4F:
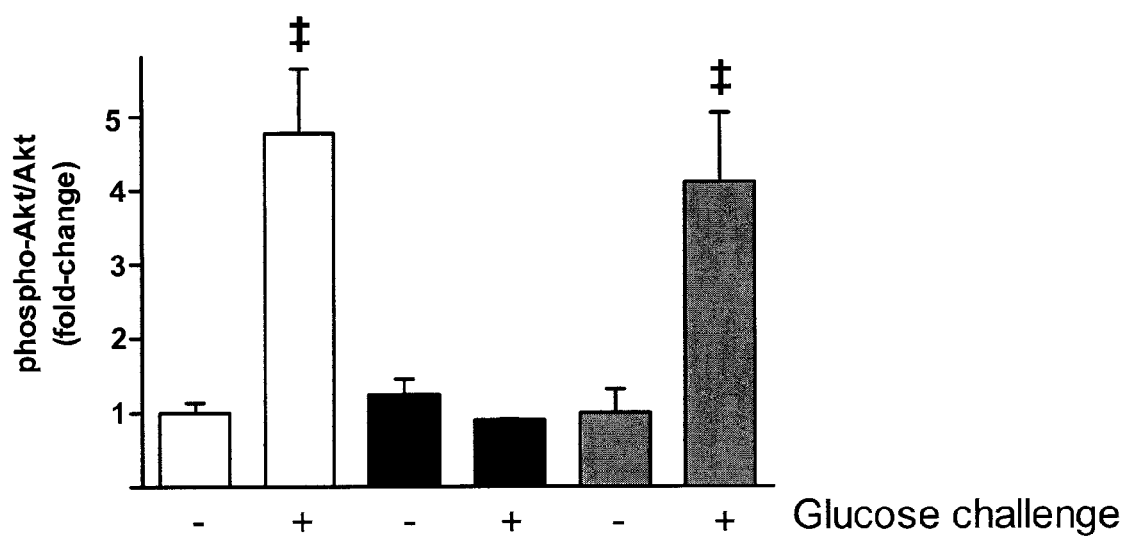
FIG. 4F is a chart showing the quantification of these blots using densitometry. Data are representative of mean ±S.E.M.; n =4-5, ‡$P<0.05$ vs. non-glucose challenged animals.

Increased homeostatic model assessment (HOMA, FIG. 4C), and greater area under the curves for both blood glucose and insulin (FIG. 4D) confirmed the development of insulin resistance in high fat fed rats. Treatment of high fat fed rats with SS-31 completely blocked the development of insulin resistance (FIGS. 4C and 4D). To further assess insulin sensitivity, the phosphorylation state of the insulin signaling protein Akt in skeletal muscle from animals was measured after a 10 h fast or 1 h after receiving an oral glucose load. In response to glucose ingestion, Akt phosphorylation increased ~5-fold in skeletal muscle of chow-fed controls but was unchanged in high fat fed rats (FIGS. 4E and 4F), confirming the presence of insulin resistance at the level of insulin signaling. Treatment of high fat fed rats with SS-31 completely preserved Akt phosphorylation in response to glucose ingestion (FIGS. 4E and 4F), again indicating preservation of insulin sensitivity. Thus, administration of a mitochondrial-targeted antioxidant, such as the aromatic-cationic peptides of the invention, prevents insulin resistance that develops in rats fed a high fat diet. As such, administration of the aromatic-cationic peptides of the present invention is useful in methods of preventing or treating insulin resistance in mammalian subjects.

Example 4

Mitochondrial Dysfunction in Human Subjects

To strengthen the link between mitochondrial-derived changes in intracellular redox environment and insulin resistance, and to see if the same phenomena is translatable to humans, the control of mitochondrial $H_2O_2$ emission and respiration in permeabilized skeletal myofiber bundles obtained by muscle biopsy from lean, insulin sensitive (BMI=21.6±1.2 kg·m$^{-2}$, HOMA=1.2±0.4) and obese, insulin resistant (BMI=43.0±4.1 kg·m$^{-2}$, HOMA=2.5±0.7, P<0.05) male human subjects was measured.

Eight healthy men (ages 18-31 y) of mixed race were recruited to participate in this investigation: five were classified as lean (BMI≦24.9 kg/m$^2$) and three were classified as morbidly obese (BMI≧35 kg/m$^2$). All participants were non-smokers with no history of metabolic disease. None of the subjects had any diseases or were taking any medications known to alter metabolism. On the day of the experiment, subjects reported to the laboratory following an overnight fast (approximately 12 h). A fasting blood sample was obtained for determination glucose and insulin (Labcorps). Height and body weight was recorded and skeletal muscle biopsies were obtained from lateral aspect of vastus lateralis by the percutaneous needle biopsy technique under local subcutaneous anesthesia (1% lidocaine). A portion of the biopsy samples were flash frozen in liquid $N_2$ for protein analysis, and another portion used to prepare permeabilized fiber bundles.

Figure 5A:
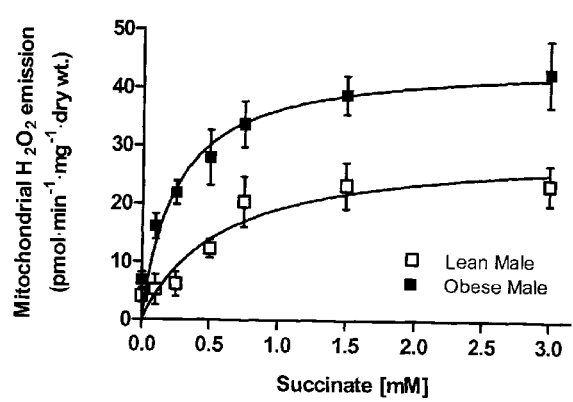
FIGS. 5A-F are a series of graphs showing the oxidation state of muscle tissues from lean and obese human subjects.
Figure 5B:
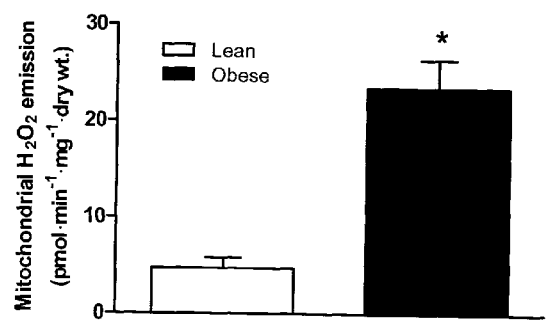
Figure 5D:
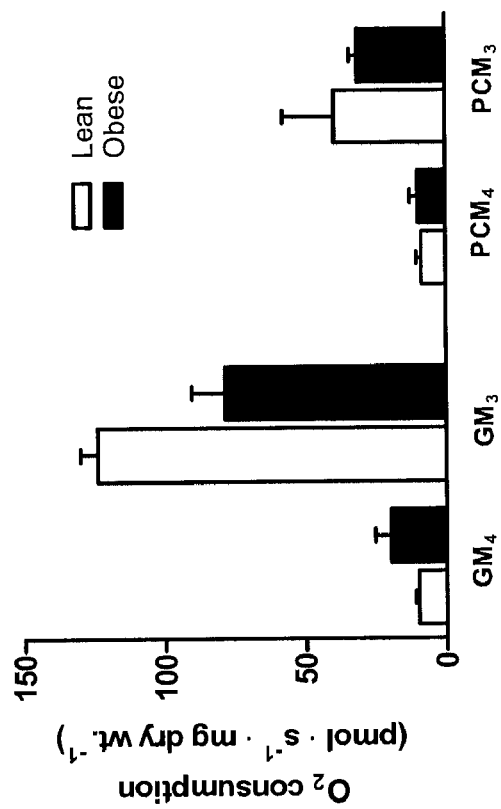
Figure 5C:
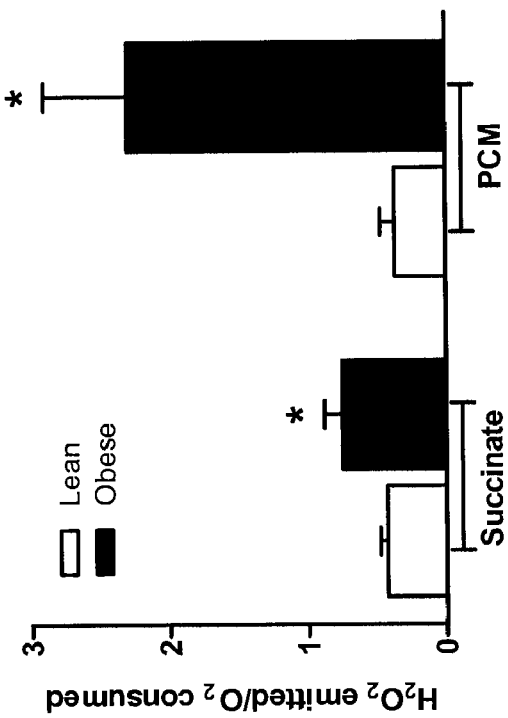
Figure 5E:
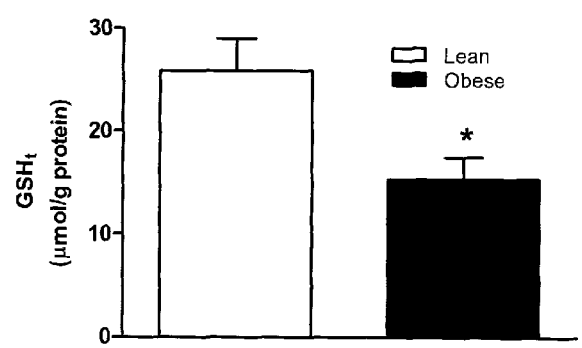
Figure 5F:
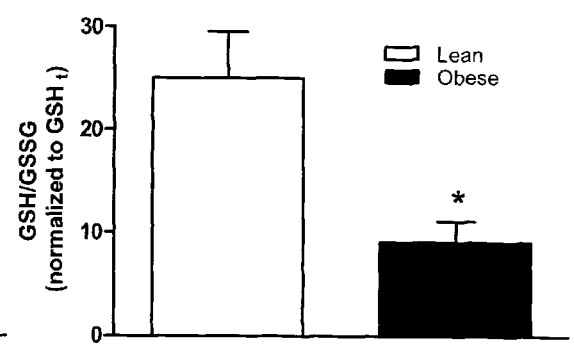

Results. Mitochondrial $H_2O_2$ emission was ~2-fold higher in obese versus lean in response to titration of succinate (FIG. 5A) and nearly 4-fold higher during basal respiration supported by fatty acid (FIG. 5B). Despite the difference in $H_2O_2$ emission, basal $O_2$ utilization was similar between lean and obese subjects (FIG. 5C); consequently, the rate of mitochondrial free radical leak was ~2-fold higher during glutamate/malate/succinate and >4-fold during palmitoyl-carnitine supported basal respiration (FIG. 5D). Maximal ADP-stimulated $O_2$ consumption was ~35% lower in permeabilized myofibers from the obese subjects during respiration supported by the complex I substrates glutamate/malate (FIG. 5C), consistent with the overall reduced skeletal muscle respiratory capacity associated with obesity. Finally, similar to rats fed a high fat diet, both total cellular GSH content and the GSH/GSSG ratio were ~50% lower in skeletal muscle of obese humans (FIGS. 5E and 5F), indicative of both an overall lower redox buffer capacity and a decidedly more oxidized intracellular redox environment.

In summary, these findings collectively establish mitochondrial ROS emission and the resulting shift to a more oxidized skeletal muscle redox environment as an underlying cause of high fat diet-induced insulin resistance. An increase in the $H_2O_2$ emitting potential of mitochondria appears to be a primary factor contributing to this shift in redox environment. Thus, administration of a mitochondrial-targeted antioxidant such as the aromatic-cationic peptides of the invention, either prevents or compensates for the metabolic dysfunction that develops with over nutrition. As such, administration of the aromatic-cationic peptides of the present invention is useful in methods of preventing or treating insulin resistance in human subjects.

Example 5

Prevention and Treatment of Insulin Resistance by Aromatic-Cationic Peptides of the Invention in the Zucker Rat Model To further demonstrate the prevention of insulin resistance on the one hand, and treatment of insulin resistance on the other hand, the aromatic-cationic peptides of the invention are tested on the fatty (fa/fa) Zucker rat, a model of diet-induced insulin resistance. Compared with the 6 wk high fat fed Sprague-Dawley rat model (as used in Examples 1-3), the fatty Zucker rats develop a much greater degree of obesity and insulin resistance. As in the high fat fed rats, mitochondrial dysfunction (increased oxidant emitting potential) is also evident in permeabilized fibers from fatty Zucker rats.

First, to examine the effects of the aromatic-cationic peptides of the invention on prevention of insulin resistance, young Zucker rats (~3-4 weeks of age) are administered SS-31 for approximately 6 weeks. As these young rats do not yet exhibit signs or symptoms of insulin resistance, they provide a useful model for assessing the efficacy of methods of preventing insulin resistance. SS-31 (1.0-5.0 mg/kg body wt) is administered to the rats via i.p. or oral administration (i.e., drinking water or gavage).

It is predicted that SS-31 administration will attenuate or prevent the development of whole body and muscle insulin resistance that normally develops in the fatty (fa/fa) Zucker rat. Measured outcomes include body weight, fasting glucose/insulin/free fatty acid, glucose tolerance (OGTT), in vitro muscle insulin sensitivity (incubation), markers of insulin signaling (Akt-P, IRS-P), mitochondrial function studies on permeabilized fibers (respiration, $H_2O_2$ emission), markers of intracellular oxidative stress (lipid peroxidation, GSH/GSSG ratio, aconitase activity) and mitochondrial enzyme activity. A comparison is made between control rats and fa/fa rats administered SS-31. Controls include wild-type and fa/fa rats not administered SS-31. Successful prevention of insulin resistance by the aromatic-cationic peptides of the invention is indicated by a reduction in one or more of the markers associated with insulin resistance or mitochondrial dysfunction enumerated above.

Second, to examine the effects of the aromatic-cationic peptides of the invention on treatment of insulin resistance, Zucker rats (~12 weeks of age) are administered S S-31 for approximately 6 weeks. As these rats show signs of obesity and insulin resistance, they provide a useful model for assessing the efficacy of methods of treating insulin resistance. SS-31 (1.0-5.0 mg/kg body wt) is administered to the rats via i.p. or oral administration (i.e., drinking water or gavage).

It is predicted that SS-31 administration will ameliorate or reduce whole body and muscle insulin resistance that normally develops in these older fatty (fa/fa) Zucker rats. Measured outcomes include body weight, fasting glucose/insulin/free fatty acid, glucose tolerance (OGTT), in vitro muscle insulin sensitivity (incubation), markers of insulin signaling (Akt-P, IRS-P), mitochondrial function studies on permeabilized fibers (respiration, $H_2O_2$ emission), markers of intracellular oxidative stress (lipid peroxidation, GSH/GSSG ratio, aconitase activity) and mitochondrial enzyme activity. A comparison is made between control rats and fa/fa rats administered SS-31. Controls include wild-type and fa/fa rats not administered SS-31. Successful treatment of insulin resistance by the aromatic-cationic peptides of the invention is indicated by a reduction in one or more of the markers associated with insulin resistance or mitochondrial dysfunction enumerated above.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

Other embodiments are set forth within the following claims.

What is claimed is:

1. A method for reducing the risk, lessening the symptoms, or delaying the outset of insulin resistance in a mammalian subject in need thereof, comprising administering to the mammalian subject a therapeutically effective amount of the peptide D-Arg-2'6'Dmt-Lys-Phe-NH$_2$ (SS-31).

2. The method of claim 1, wherein the subject is a human.

3. The method of claim 1, wherein the subject is suffering from diet-induced insulin resistance.

4. The method of claim 1, wherein the insulin resistance is associated with type II diabetes.

5. The method of claim 1, wherein the insulin resistance is associated with obesity.

6. The method of claim 1, wherein the insulin resistance is associated with coronary artery disease, renal dysfunction, atherosclerosis, hyperlipidemia, essential hypertension, or fatty liver.

7. The method of claim 1, wherein the insulin resistance is drug-induced insulin resistance.

8. The method of claim 1, wherein the peptide is administered prior to the onset of type II diabetes.

9. The method of claim 1, wherein the peptide is administered orally, topically, systemically, intravenously, subcutaneously, or intramuscularly.

10. The method of claim 1, further comprising the step of identifying the mammalian subject in need of a therapeutically effective amount of the peptide D-Arg-2'6'Dmt-Lys-Phe-NH$_2$ (SS-31).

11. The method of claim 1, further comprising monitoring the mammalian subject for the therapeutic effects of the peptide D-Arg-2'6'Dmt-Lys-Phe-NH$_2$ (SS-31).

12. The method of claim 1, wherein the therapeutically effective amount of the peptide D-Arg-2'6'Dmt-Lys-Phe-NH$_2$ (SS-31) provides a concentration of peptide in a target tissue of about $10^{-8}$ to $10^{-6}$ molar.

* * * * *